(12) United States Patent
Patnaik et al.

(10) Patent No.: US 12,133,987 B2
(45) Date of Patent: Nov. 5, 2024

(54) FEEDTHROUGHS

(71) Applicant: Morgan Advanced Ceramics, Inc., New Bedford, MA (US)

(72) Inventors: Abhishek S. Patnaik, Lexington, MA (US); John Antalek, East Freetown, MA (US); Mark Schmeckpeper, Albuquerque, NM (US); Abhaya Bakshi, Westford, MA (US); Robert MacKinnon, Carver, MA (US)

(73) Assignee: Morgan Advanced Ceramics, Inc., New Bedford, MA (US)

( * ) Notice: Subject to any disclaimer, the term of this patent is extended or adjusted under 35 U.S.C. 154(b) by 861 days.

(21) Appl. No.: 17/253,251

(22) PCT Filed: Apr. 18, 2019

(86) PCT No.: PCT/EP2019/060196
§ 371 (c)(1),
(2) Date: Dec. 17, 2020

(87) PCT Pub. No.: WO2019/129893
PCT Pub. Date: Jul. 4, 2019

(65) Prior Publication Data
US 2021/0146142 A1 May 20, 2021

(30) Foreign Application Priority Data
Jun. 19, 2018 (EP) .................................. 18178542

(51) Int. Cl.
*H01B 3/12* (2006.01)
*A61N 1/375* (2006.01)

(52) U.S. Cl.
CPC ......... *A61N 1/3754* (2013.01); *A61N 1/3758* (2013.01); *H01B 3/12* (2013.01)

(58) Field of Classification Search
CPC ... H01B 3/12; H01B 3/00; H01B 3/08; H01B 17/265; H01B 17/301; H01B 17/303;
(Continued)

(56) References Cited

U.S. PATENT DOCUMENTS

| 5,272,283 A | 12/1993 | Kuzma |
|---|---|---|
| 5,434,358 A | 7/1995 | Glahn et al. |

(Continued)

FOREIGN PATENT DOCUMENTS

| CN | 103842024 A | 6/2014 |
|---|---|---|
| EP | 0869553 A2 | 10/1998 |

(Continued)

OTHER PUBLICATIONS

Green, Rylie A., et al., "Integrated electrode and high density feedthrough system for chip-scale implantable devices", Biomaterials, vol. 34, No. 26 pp. 6109-6118.

*Primary Examiner* — Angel R Estrada
(74) *Attorney, Agent, or Firm* — Servilla Whitney LLC

(57) ABSTRACT

There is provided a feedthrough including a ceramic body; and a plurality of electrical conductors embedded in the ceramic body. Wherein the density of the electrical conductors exceeds 1 conductor per 23 thou$^2$ (14,839 μm$^2$) through a planar cross-section of the ceramic body.

19 Claims, 23 Drawing Sheets

(58) Field of Classification Search
CPC ........ H01B 17/26; H01B 17/00; H01B 19/00;
A61N 1/3754; A61N 1/3758; A61N
1/3752; H01F 27/04; H01F 27/02; H01F
27/022; H01H 9/02; H01H 9/0264
USPC ....... 174/98, 142, 138 R, 139, 138 F, 137 R,
174/143, 152 GM, 262, 251, 261, 255,
174/50.5; 439/909, 668; 607/36, 37,
607/119; 361/600, 601, 302, 30.1, 306.1
See application file for complete search history.

(56) References Cited

U.S. PATENT DOCUMENTS

| | | | |
|---|---|---|---|
| 7,480,988 B2 | 1/2009 | Ok et al. | |
| 7,839,620 B2 * | 11/2010 | Iyer | A61N 1/3754 361/313 |
| 7,988,507 B2 | 8/2011 | Darley et al. | |
| 7,989,080 B2 | 8/2011 | Greenberg et al. | |
| 8,163,397 B2 | 4/2012 | Ok et al. | |
| 8,277,227 B2 | 10/2012 | Darley et al. | |
| 8,588,915 B2 * | 11/2013 | Iyer | A61N 1/3754 333/182 |
| 8,670,829 B2 * | 3/2014 | Morioka | H05K 3/4046 607/37 |
| 8,698,006 B2 | 4/2014 | Bealka et al. | |
| 8,706,228 B2 * | 4/2014 | Iyer | A61N 1/3754 607/36 |
| 8,841,558 B2 * | 9/2014 | Morioka | A61N 1/3754 174/255 |
| 9,698,662 B2 | 7/2017 | Sugihara et al. | |
| 2012/0306128 A1 | 12/2012 | Parker et al. | |
| 2013/0032382 A1 | 2/2013 | Morioka et al. | |
| 2014/0036409 A1 | 2/2014 | Stevenson et al. | |

FOREIGN PATENT DOCUMENTS

| | | |
|---|---|---|
| EP | 2437850 A1 | 4/2012 |
| TW | 452844 B | 9/2001 |
| WO | 2010141100 A1 | 12/2010 |

* cited by examiner

Fig. 3
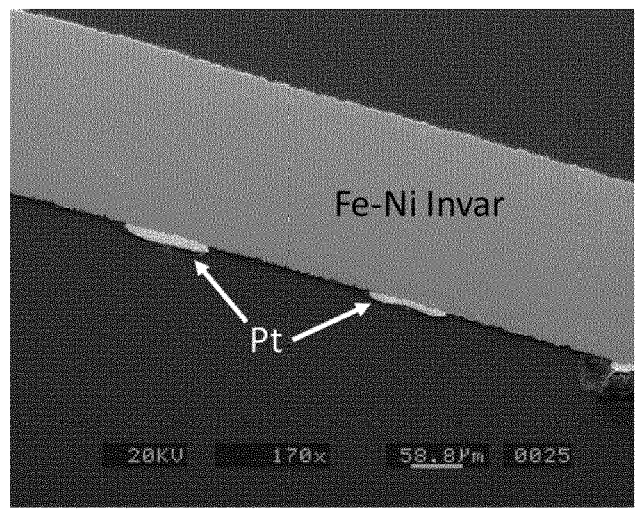
(a)
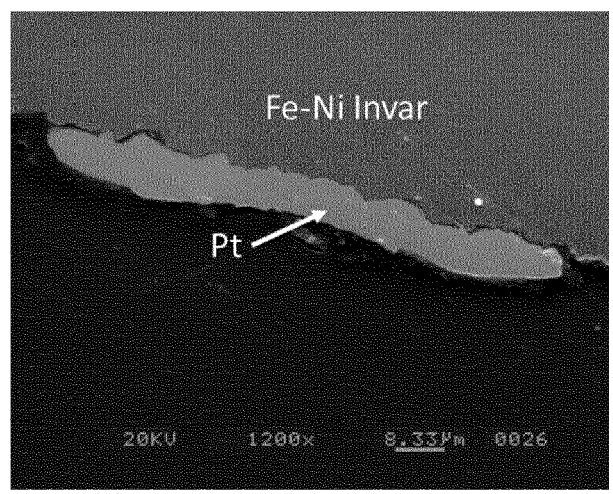
(b)
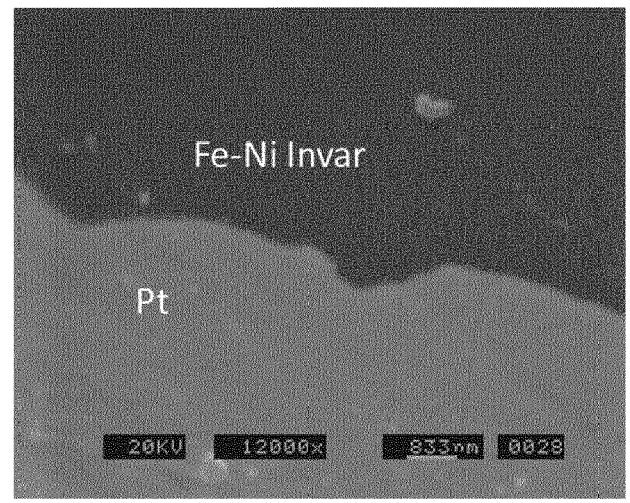
(c)

Fig. 6
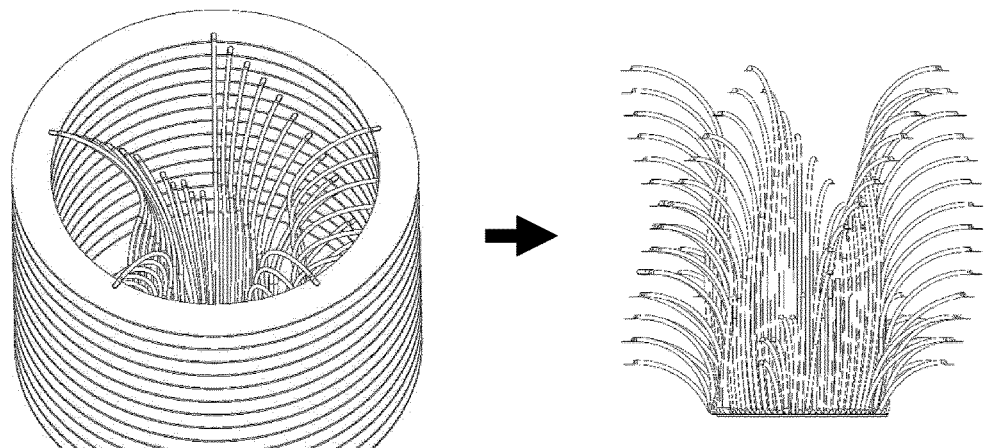
(a) (b)
(c) (d)
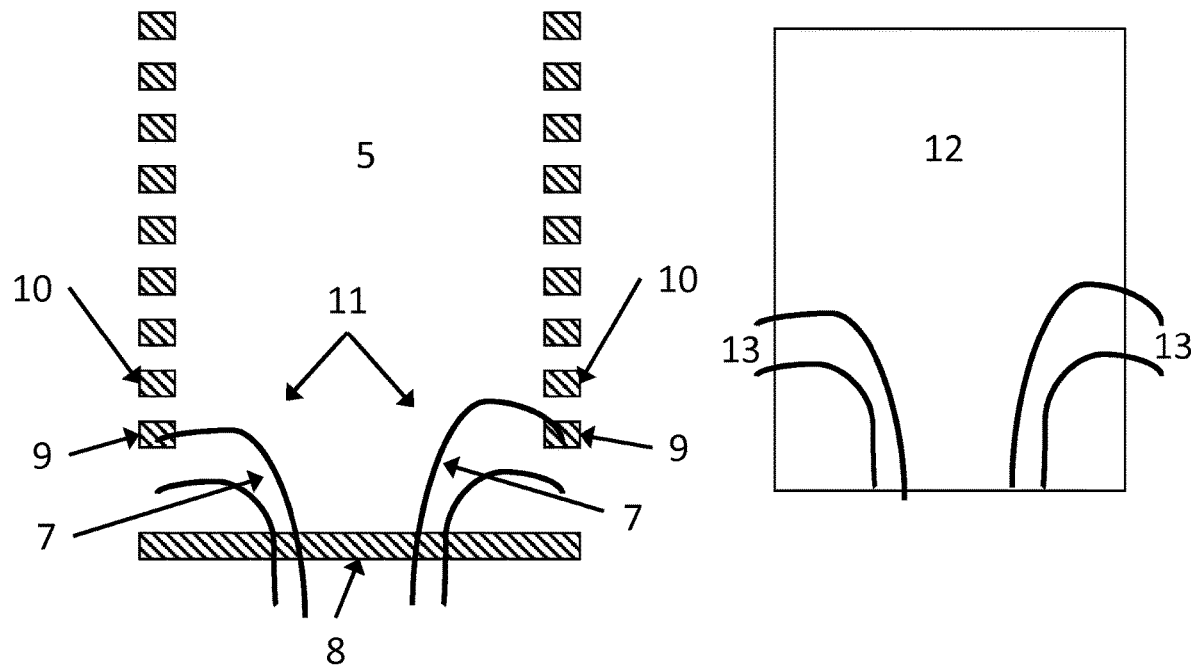

Fig. 16
(Prior art)
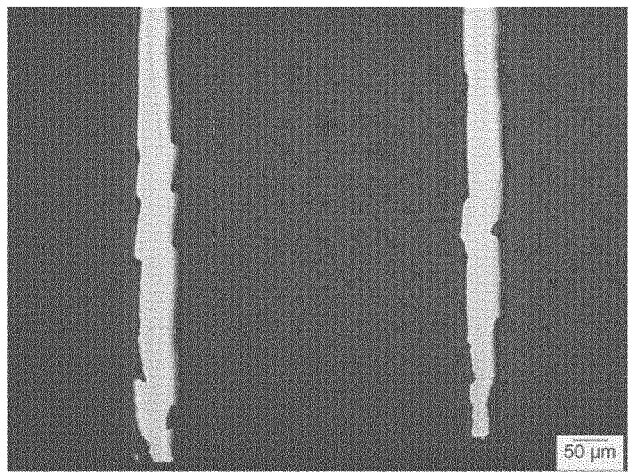
(a)
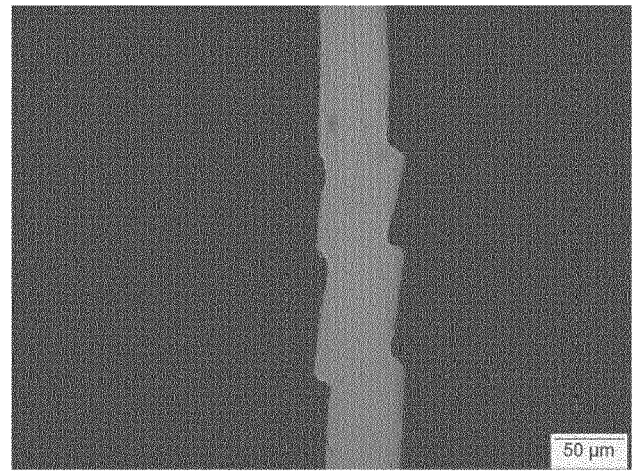
(b)
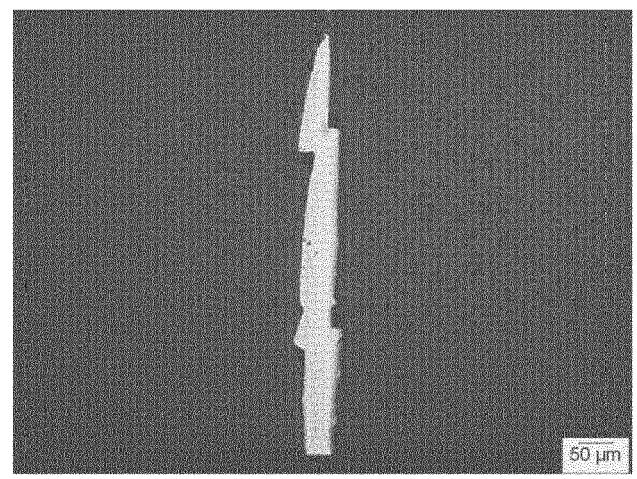
(c)

Fig. 17
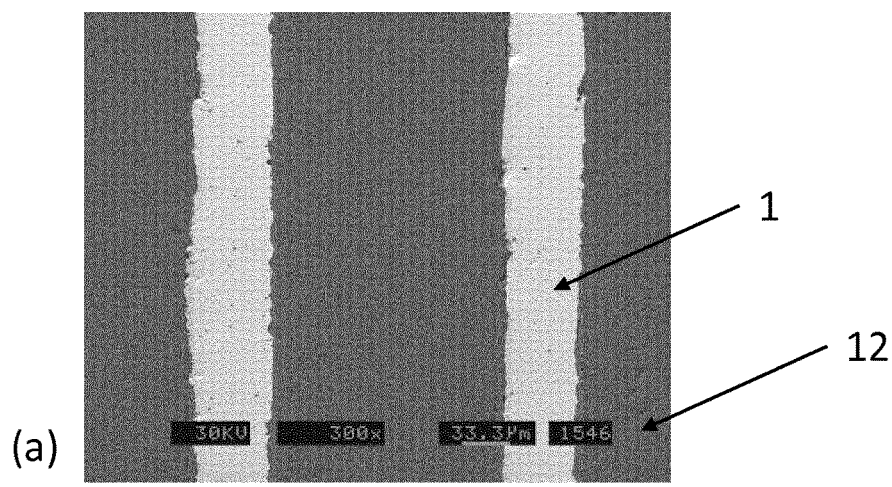
(a)
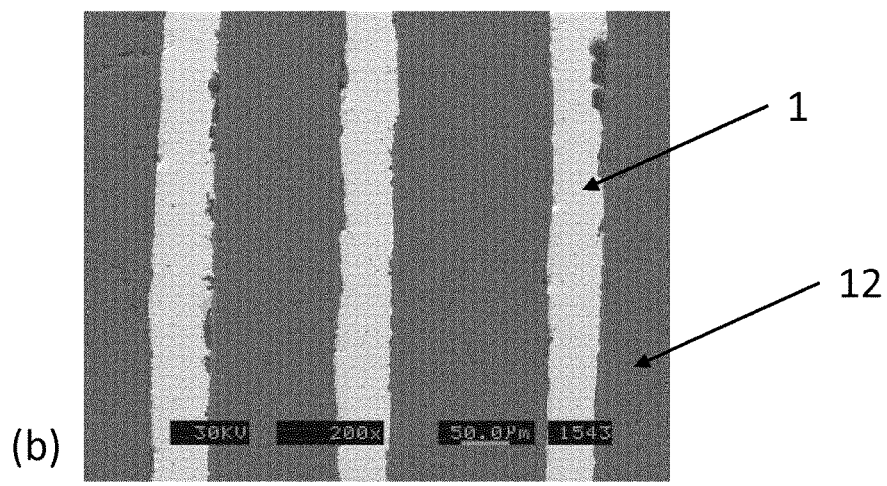
(b)
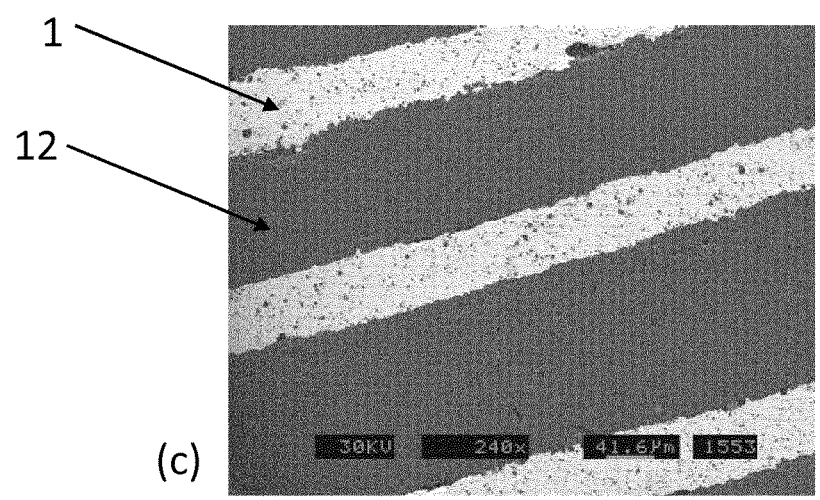
(c)

FEEDTHROUGHS

CROSS-REFERENCE TO RELATED APPLICATIONS

This application is the National Stage entry of PCT/EP2019/060196, filed on Apr. 18, 2019, which claims priority to European Patent Application number 18178542.9, filed Jun. 19, 2018, the entire disclosures of which are hereby incorporated by reference herein.

FIELD

This disclosure relates to feedthroughs including electrical conductors at least in part embedded in a ceramic matrix. The present disclosure further provides methods of making such feedthroughs.

BACKGROUND

Metal ceramic assemblies are required for many applications, and have found particular use in applications where one or more electrical conductors are required to pass through a ceramic insulator to provide one or more electrically conductive connections from one surface of the ceramic insulator to another surface of the ceramic insulator. Such an arrangement of a conductor passing through an insulator is commonly known as a "feedthrough". Such arrangements are widely used, for example in medical, aerospace, transportation, communication and power tube (e.g. x-ray, radio frequency) applications, and the present disclosure is not limited to any one application.

While the present disclosure is generally applicable, its impact can be seen by reference to a particularly demanding application, namely the provision of braze-free hermetic feedthroughs for medical applications.

Electronic biomedical implants are being increasingly used to diagnose, prevent and treat diseases and other conditions. Such implanted devices are typically housed in hermetic packages that incorporate electrical feedthroughs for signal transfer between the housed electronic device and the environment. Such implantable devices, especially those that interface with the human nervous system, the cochlea, or the retina, require a multiplex of leads in a very small feedthrough.

Biocompatible metal ceramic feedthrough systems may be considered to be the most reliable choice for such devices owing to their inertness (e.g. biocompatibility) and longevity (e.g. biostability).

For certain therapies, it is desirable to increase the number of electrical conductors (which have many names in the art of feedthroughs including: leads, pathways, pins, wires, and vias) in the feedthroughs to increase the number of I/O signals. However, it is simultaneously desirable to decrease the size of the feedthrough as it is not desirable to implant a large device (including a large feedthrough) in to the human or animal body. In particular, it is desirable to reduce the invasiveness of the implantation surgeries and/or the nature of the placement of the device for the target therapy requires a small device, such as retinal implants. When the device design requires both a large number of conductors (i.e. high pin count) and a small size feedthrough, conventional feedthrough manufacturing techniques are no longer viable.

It is therefore desirable to increase the density of the conductors within feedthroughs. However, existing technologies have limits as to the spacing of conductors within the feedthrough. Therefore, until now, it has been necessary either to make the feedthrough larger (and therefore also a device including the feedthrough) or to reduce the number of I/O signals, both of which are undesirable.

It is a non-exclusive aim of the present disclosure to provide cost effective miniaturization of a biocompatible, biostable co-fired feedthrough. It is a further non-exclusive aim of the present disclosure to provide novel three-dimensional architectures. It is an additional non-exclusive aim of the present disclosure to provide a cost effective method of manufacture of feedthroughs.

Conventional gold brazed feedthrough technologies are capable of providing conductor-to-conductor spacings as close as 0.022 inch (") using 0.004" diameter wires with gold braze rings. Additionally, using manual techniques of placing electrically conductive wire (e.g. pins) with gold braze rings into preformed (e.g. drilled, pressed, stamped) holes within an electrically insulative member (typically a high purity alumina ceramic) to construct the feedthrough with a high number of leads is costly and increases the opportunity for errors leading potentially to high scrap rates. Besides the challenge of constructing such a feedthrough by hand, a current practice of utilizing a gold braze ring to assist in achieving a hermetic bond between the metallic pin and the insulator is design limiting. The thickness of this gold ring adds a design constraint and limits the proximity that the conductors can be placed in proximity to each other. This limits the density of the conductors and therefore constrains the degree to which the feedthrough can be miniaturized.

It has been proposed to make feedthroughs using a tape casting/layer by layer stacking process. Here thin ceramic tapes are first processed to have through holes which are then filled with a metal or ceramic-metal ("cermet") ink. These tapes are then aligned and stacked together and subsequently co-fired to produce a feedthrough with the aligned filled holes forming the conductive pathways. This technology has dimensional limitations to the feature size and shape (in this example holes that are cut in individual tapes). Also, since the holes are filled with a metal/cermet ink, there can be spillage around the surface edges, which tend to protrude out from the conductive via-path in the sintered state. This reduces the effective conductive pathway to conductive pathway distance to less than the design separation to assure insulative isolation, causing possible areas for electrical failure (e.g. an electrical short or arc) of the device. Such spillage may also act as a structural defect which may elongate if thermally cycled leading to loss in hermeticity and potential delamination. The manufacturing of feedthroughs with this technology is also process intensive thus increasing cost. Further, the use of particulate ink (metal/cermet) in this technology leads to potential issues during the I/O termination/connections to other electronic components especially in the high density or miniature scale devices. Also, the use of a non-metal filler within the conductive pathway increases the electrical resistance of the pathway (e.g. reducing the electrical conductivity) reducing the electrical efficiency of the device, requiring more energy than would otherwise be necessary, resulting either in the need for a larger battery to achieve the required device lifetime (thus constraining the miniaturization of the device), or resulting in reduced lifetime for a given battery size (thus limiting the lifetime of the device).

Some known examples of feedthroughs and techniques for providing feedthroughs for such medical application include: —

U.S. Pat. No. 8,698,006 (US'006) discloses feedthroughs including:
a. an insulative component; and
b. first and second conductors electrically isolated from each other by the insulative component.

A density of 1 conductor per 24 thou$^2$ (i.e. 0.000024 square inches or 15483 µm$^2$) is disclosed in FIG. 19.

The method of US'006 includes forming a feedthrough by:
a. providing a first insulative component with at least one bonding surface;
b. providing a second insulative component;
c. disposing a conductor between the first and second insulative components and along at least a portion of the bonding surface;
d. bonding the first and second insulative components at the bonding surface; and
e. exposing a portion of the conductor.

A problem with the method and feedthroughs of US'006 is that the pressing force causes the conductor to deform, forming a tortuous (e.g. zigzag) profile that reduces the conductive efficiency of the conductive pathway. Also, without a method to fix the conductors in place during the pressing operation, the conductors can move, resulting in positional inaccuracies of the conductive paths, complicating subsequent attachment of the conductive paths to a device and/or to leads. Further, producing a hermetic bond between the insulative component and the electrically conductive wire becomes increasingly difficult as the size of the diameter of the wire is increased above 0.003 inch, effectively limiting the maximum size of the wire that can be used. Lastly, the minimum thickness of the thinnest green ceramic plates that can be produced and placed between the rows of pins, limits the minimum spacing of these rows of pins to each other to 0.016" (0.406 mm).

U.S. Pat. No. 7,988,507 (US'507) discloses a feedthrough for an implantable medical device including:
an electrically insulating body including a first surface and a second surface; and
one or more electrically conductive structures configured to contiguously extend through and be embedded within said electrically insulating body, such that each of said one or more electrically conductive structures are circumferentially covered by said electrically insulating body, such that opposing ends of said at least one electrically conductive structures are exposed, and such that said at least one electrically conductive structures extend beyond at least the first or second surface,
wherein the one or more electrically conductive structures include an electrically conductive metal or metal alloy and have a thickness of a film of the same electrically conductive metal or metal alloy.

US'507 also discloses a method of forming an electrically conducting feedthrough including the steps of:
(i) forming an electrically conductive structure including a sacrificial component and non-sacrificial component;
(ii) coating at least a portion of the non-sacrificial component with a relatively electrically insulating material; and
(iii) removing at least a portion of the sacrificial component from the electrically conductive structure,
to form an electrically conductive structure including a sacrificial component and non-sacrificial component included stamping a foil or cutting a foil using electrical discharge machining.

The coating step (ii) includes moulding a coating of the insulating material on and/or around the conductive structure and in a preferred embodiment used powder injection moulding (PIM) to mould the insulating material around a desired portion of the conductive structure.

Problems with the process of US'507 include that for medical applications noble metals (e.g. platinum) are the desired conductors and the sacrificial part of the platinum foils used results in waste material requiring expensive recycling. Further, when stamping platinum from a foil the individual conductors can be embrittled in the stamping process, limiting the diameter of conductors that can be formed. Further still, a stamping process requires the use of precision stamping dies for each geometry of feedthrough. Yet further, when sections of a foil are removed within a foil, the remaining sections within the foil can sag or flex because residual stresses have been relieved from the foil by removing material and because the removal of mass has reduced the stiffness of the remaining foil sections. This sagging by itself, or deflection of the remaining material when subjected to the subsequent molding pressure, can result in positional inaccuracies of the conductive paths, complicating subsequent attachment of the conductors to a device and/or to leads.

The methods of US'507 and US'006 limit the arrangement of conductors to essentially parallel layers of conductors. The limitation to essentially parallel arrangements of conductors limits the conductor pathways that can be achieved. This means that additional circuitry external of the feedthrough may be required.

US2013/0032382 (US'382) discloses a hermetic feedthrough for an implantable device, including:
Stacked sheets of electrically insulative ceramic alumina, each sheet containing a hole(s) that are substantially aligned with one another to form a conductive path through the sheets via the holes filled with an electrically conductive substance; the sheets and the conductive substance having a co-fired bond between the sheets and that hermetically seals the hole.

US'382 also discloses that the resulting tortuous (e.g. staggered, serpentine, zigzag) path of the resulting vias improves the hermetic seal of the feedthrough by better impeding fluid from seeping along the via. However, this benefit may be offset by the same tortuous path increasing resistance to electrical current, decreasing the efficiency of the device to which the feedthrough is attached versus an otherwise straight via.

US'382 limits its examples to holes of 0.006"-0.008" (152 µm-203 µm) diameter, with via lengths of 0.042" to 0.066" (1067 µm to 1676 µm) length with pitch of ~0.0181" (460 µm) having passed a He leak test. However, only a hole of 0.008" (203 µm) diameter and of length 0.042" (1067 µm) and a minimum pitch of ~0.028" (711 µm) was illustrated to exhibit no dye penetration.

A minimum pitch of 18.1 thou (0.0181 inch; 460 µm) corresponds to 1 conductor per 328 thou$^2$.

U.S. Pat. No. 7,480,988 (US'988), U.S. Pat. No. 7,989,080 (US'080), U.S. Pat. No. 8,163,397 (US'397), and U.S. Pat. No. 5,272,283 (US'283) describe feedthroughs having metal tubes (acting as the conducting path) co-fired to a ceramic insulator whereby a (hermetic) seal by compression of the tube is achieved as the ceramic shrinks when the assembly is fired and then allowed to cool. Although perhaps effective when using tubes with diameters exceeding >0.040 inch (1016 µm) and ceramic sheet at least 0.70 inch (17.78 mm) thick, smaller tube diameters are impractical, limiting the smallest possible feedthrough geometry.

US'283 discloses that it is not possible to produce a co-fired feedthrough with a high number of conductive pathways (cited as typically 10-22).

US'988, US'080, and US'397 also disclose that feedthroughs relying upon ceramic insulators consisting of 92% or 96% alumina with significant glass content. However the glass is susceptible to hydroxide etching. This etching chemical reaction may result when the ceramic/glass feedthrough is exposed to an aqueous chloride environment such as found in the human body. Further discussion of this phenomenon is described in U.S. Pat. No. 9,698,662.

US'988, US'080, and US'397 also describe a method of producing a hermetic feedthrough consisting of a ceramic sheet less than 0.040" (1.02 mm) thick containing drilled blind holes into which metal wires with diameters of less than 0.010" (0.256 mm) are inserted and then subsequently co-fired to achieve the hermetic seal, however, no hermetic values are presented. After firing the ceramic is lapped on the blind hold side to expose the wires for the purpose of achieving an electrically conductive pathway through the insulating ceramic. A helium leak test is performed, although the documents are silent whether a dye penetrant test has been conducted. Singulation (dicing) then follows to form the exterior periphery of the individual feedthroughs. The documents are silent regarding the nearest spacing of the resulting conductors that has been achieved by this approach. The documents are also silent regarding the insertion method employed. It is reasonable to anticipate that the method of pin insertion is manual, requiring labor to place and fixturing to hold such small, lightweight, delicate pins in place during the co-sintering operation. This also potentially requires high labor costs and results in poor yields. There is a practical limit to how close pins can be placed to each other using manual techniques. Further, grinding of the fired ceramic to expose the metal wire (in order to attach to electrical connection pathways) adds cost. Yet further, the examples are limited to a parallel array of wires.

U.S. Pat. No. 8,277,227 (US'227) discloses fabrication of feedthroughs by inserting conductive pins (wires) into an unsintered (or 'green') ceramic and then co-firing (such as described by US'988, US'080, and US'397). The hand assembly of US'227 leads to inaccuracies, is time consuming (labor intensive and therefore relatively expensive), and can result in unsatisfactory leak rates on testing and result in poor yields. It seems that the methods of US'988, US'080, and US'397 also include such hand assembly. Additionally, the resulting position of the co-fired pins lacks precision as it is dependent on the manual process. This can present subsequent difficulties in integration of the I/O in an implantable device. This lack of precision also necessarily limits the maximum achievable density of pins within a feedthrough.

US'227 also discloses that cochlear implants typically rely upon feedthroughs containing 22-24 conductive pins with a desire to increase the number of pins while reducing the size of feedthrough. A high degree of labour intensity and specialisation such as backface grinding in order to expose the wire can raise manufacturing problems. Thus, US'227 discloses a method to achieve such a co-fired feedthrough which is reliant upon a thin conductive film to form the conductive pathways that are not dependent upon such labor intensive processes to place the wires. However, US'227 provides few details of the hermeticity values and dye penetrant results obtained, size boundaries of the conductive pathways, spacing boundaries between pathways, parallelism or positional accuracy of the conductive pathways.

US'227 does provide the relationship: $H=f(L, 1/A, 1/t)$ where H represents hermeticity, L is the length of the electrically conductive element measured form the first face to the second face of the insulative portion of the feedthrough, A is the cross-sectional area of the electrically conductive element, and t is the time that the interface is exposed to the fluid such as body fluid. The formula implies feedthroughs with thick cross sections with small conductive via diameters (or cross sections if the conductive pathway is not circular in cross section) will have improved hermeticity versus thin feedthroughs with large diameter conductive pathways.

US'227 discloses a thickness of the conductive members being 0.040" to 0.070" (1.02 mm to 1.78 mm) but does not disclose the width of the conductors, hermeticity or dye penetrant results nor thickness of the feedthrough, nor resulting positional accuracy or closest spacing of the conductive elements. However, US'227 discloses the use of shaped (e.g. stepped or screw-thread shape) conductive members to improve hermeticity, it must, therefore, be assumed that without shaping the conductive members the hermeticity is insufficient.

SUMMARY

It is a non-exclusive object of the present specification to provide improved feedthroughs. The improved feedthroughs may address, at least partially, the disadvantages realised in the prior art (as discussed above). The improved feedthroughs of this specification may be provided by new feedthrough manufacturing methods disclosed herein. These feedthrough manufacturing methods may address, at least partially, the disadvantages realised in the prior art (as discussed above).

It is a (non-exclusive) aim of this specification to provide methods capable of forming hermetic feedthroughs having a small inter-conductor separation; methods capable of providing arrangements of conductors not limited to layers; methods that can be repurposed without the need for precision stamping dies; methods that can produce non-tortuous conductive pathways; and/or methods that can provides an array of conductors that are accurately and/or precisely positioned.

It is also a (non-exclusive) aim of this specification to provide hermetic feedthroughs having a small inter-conductor separation; feedthroughs including conductors not limited to layers; feedthroughs including non-tortuous conductors; and/or feedthroughs including an array of conductors that are positioned accurately and/or precisely.

The feedthroughs may be biocompatible. The feedthroughs may be hermetic. In particular, the feedthroughs may be implantable with a human or animal body. Advantageously, the feedthrough may be able to withstand the chemical reactions that can occur within the human body. For example, the feedthrough may remain hermetic for the life of the implant. For example from one to 20 years or more.

It is also a (non-exclusive) aim of this specification to provide feedthroughs having straight, solid, metal wire of a range of diameters. Larger diameter wires can provide increased electrical conductivity efficiency.

It is also a (non-exclusive) aim of this specification to provide methods which do not rely upon insertion of individual wires into a green ceramic nor post grinding the fired ceramic to expose the wire to the feedthrough surface (which may be costly). In other words, it is (non-exclusive) aim to automate the placement of the conductors. Further, it is a (non-exclusive) aim to produce thin profiles and place wires easily in close proximity to each other with accurate positioning.

It is a further (non-exclusive) aim of this specification to provide methods which can be implemented by robot (instead of manually). Such implementation can reduce labour costs and improve device yield. Further, robotic construction may be particularly suited to the use of thin, closely packed conductors and the provision of miniature feedthroughs.

It is a further (non-exclusive) aim of this specification to eliminate the need to use gold braze rings around the conductors. Removing the need to use a gold braze ring can help alleviate dimensional constraints. Eliminating the ring can reduce required spacing allowing miniaturization of the feedthrough. Further, in the prior art, under certain conditions the gold can electro-migrate leading to a loss of a hermetic seal. Directly bonding the conductor to the insulator without the use of a gold braze can eliminate (or reduce the risk of) electro migration potential, this can improve the long-term hermeticity (and therefore biostability) of the feedthrough. Yet further, elimination of the need to use a gold braze ring can remove the need for a cost involved in the production of the feedthrough.

The methods disclosed herein are useful for providing high-pin count and/or miniature feedthroughs. Additionally, the methods disclosed herein are also useful for providing low-pin count feedthroughs and/or non-miniature feedthroughs. Further, whilst prior art methods of feedthrough construction permit a two-dimensional arrangement of conductors, the methods disclosed herein can enable a three-dimensional arrangement of conductors.

Further, as the methods and feedthroughs of the present specification can use solid metal wire conductors, instead of metallic paste with a ceramic additive (or alternatives), conductors with low electrical resistance can be provided within the feedthroughs. In turn this can increase device battery life or allow the use of smaller batteries. Increased battery life can reduce the number of surgeries required by reducing the number of times a medical device has to be replaced. Yet further, a conductive pathway with lower electrical resistance permits the designer of a feedthrough to specify a conductor with a smaller diameter, potentially allowing further miniaturization of the feedthrough and a smaller battery allowing further miniaturization of the implanted device.

Yet further, the methods disclosed herein can provide devices having a non-tortuous profile of the conductor. This can provide a low electrical resistance of the conductive path (preserving the ability to specify a small conductive pathway diameter), prevent or reduce the likelihood of formation of potential stress risers (that can lead to loss of a hermetic seal), and prevent or reduce the likelihood of short-circuit pathways between conductors. This contrasts with prior art methods in which wires are deformed during the feedthrough fabrication processes, which can result in a torturous (e.g. zigzag) conductive pathways or processes. Such processes typically rely upon pastes or inks which can seep between ceramic layers (e.g. tape layers) of the insulating member (thereby providing non-desirable short-circuit pathways).

A further potential benefit of the methods and devices disclosed herein is the positional accuracy of the conductive paths in contrast to prior art fabrication processes that rely upon molding pressure (e.g. compression, injection molding). In the prior art, upon application of a molding pressure conductive pathways can move or deflect. In turn, this can alter the position of the conductors complicating subsequent attachment of the feedthrough conductors to the device and/or to the leads. Movement of the pathways may also undermine the electrical resistance of the insulating member by reducing the distance between adjacent conductive pathways. To account for such movement using such processes, the minimum pathway design distance between pathways must be increased, hindering optimal miniaturize the feedthrough. Accordingly, a (non-exclusive) aim of the present disclosure is the provision of fabrication methods that do not require the application of (significant) molding pressures, which can move or deflect the conductors of a feedthrough.

It is a further (non-exclusive) aim of the present disclosure to provide a method which can be used (cost-effectively) with a range of diameters of conductors. As will be apparent, such methods may be used to provide a range of feedthroughs having a range of conductor diameters. Prior art feedthrough fabrication methods that rely on compressive force to sandwich conductive wires between green ceramic insulating sheets can experience an upper limit of wire diameter that can be successfully pressed. Feedthrough fabrication methods that rely on insertion of small diameter wires into preformed holes within an insulating ceramic can experience high labor costs and poor yields due the delicate nature of the wires that may bend during insertion. Providing methods which can be used with a variety of conductors is advantageous as small diameter wires may be required to achieve certain degree of miniaturization, while large diameter wires may be a necessity for devices that require transmission of signals of higher voltage.

STATEMENTS

Accordingly, in a first aspect of the present invention there is provided a feedthrough including:
a ceramic body; and
a plurality of electrical conductors embedded in the ceramic body,
wherein the density of the electrical conductors exceeds 1 conductor per 23 thou$^2$ (14,839 µm$^2$) through a planar cross-section of the ceramic body.

The density of the electrical conductors preferably exceeds 1 conductor per 22 thou$^2$ (14,194 µm$^2$), or exceeds 1 conductor per 21 thou$^2$ (13,548 µm$^2$), or exceeds 1 conductor per 20 thou$^2$ (12,903 µm$^2$), or exceeds 1 conductor per 19 thou$^2$ (12,258 µm$^2$), or exceeds 1 conductor per 18 thou$^2$ (11,613 µm$^2$), or exceeds 1 conductor per 17 thou$^2$ (10,968 µm$^2$), through a planar cross-section of the ceramic body. Preferably, the density of electrical conductors is no more than 1 conductor per 9 thou$^2$ (5,806 µm$^2$), or 1 conductor per 12 thou$^2$ (7,742 µm$^2$), or no more than 1 conductor per 13 thou$^2$ (8,387 µm$^2$), or no more than 1 conductor per 14 thou$^2$ (9,032 µm$^2$), or no more than 1 conductor per 15 thou$^2$, or no more than 1 conductor per 16 thou$^2$ (10, 323 µm$^2$) through a planar cross-section of the ceramic body. The density of electrical conductors may be no more than 1 conductor per 17 thou$^2$ through a planar cross-section of the ceramic body. Electrical isolation between conductors and/or the maintenance of sufficient hermeticity may be more readily achieved at lower densities.

Higher densities of the electrical conductors are generally more achievable with lower conductor diameters. However, greater conductor diameters can help to provide mechanical integrity of the feedthrough as well as meet electrical performance criteria (e.g. current carrying capacity).

The present invention also provides a combination of high density with one or more other features including, but not limited to, smaller diameter conductors; more parallel conductors; the plurality of elongate electrical conductors traverse the ceramic body in a non-coplanar relationship; and/or more uniform bulk density.

When combined with other features, the density of the conductors preferably exceeds 1 conductor per 300 thou$^2$ (193,584 μm$^2$); or exceeds 1 conductor per 250 thou$^2$ (161,290 μm$^2$); or 1 conductor per 200 thou$^2$ (129,032 μm$^2$); or 1 conductor per 150 thou$^2$ (96,774 μm$^2$); or 1 conductor per 100 thou$^2$ (64,516 μm$^2$); or 1 conductor per 50 thou$^2$ (32,258 μm$^2$) through a planar cross-section of the ceramic body.

Each of the plurality of electrical conductors may be parallel relative to each other within 2°. Further, each of the plurality of electrical conductors may be parallel to each other within 1.5°, 1°, 0.5° or 0.2°.

There is also provided a feedthrough including a plurality of electrical conductors embedded in a ceramic body, in which the plurality of elongate electrical conductors traverse the ceramic body in a non-coplanar relationship.

The plurality of elongate electrical conductors may include at least one planar array of elongate electrical conductors defining a plane, and at least one elongate electrical conductor non-parallel with said plane.

The plurality of elongate electrical conductors may include at least two groups of elongate electrical conductors, the conductors in each group being in a coplanar relationship to define a group plane, and in which the group planes of at least two of the plurality of groups are non-parallel.

The plurality of elongate electrical conductors may include at least one group of elongate electrical conductors diverging from a first region of the ceramic body to a second region of the ceramic body, the first region being smaller in area than the second region.

The ceramic body may include one or more walls extending from a base, and at least one of said plurality of elongate electrical conductors may be mounted to traverse the ceramic body from the base to said one or more walls.

At least two of said plurality of elongate electrical conductors may be mounted non-parallelly to traverse the ceramic body diverging from the base to said one or more walls.

Each of the plurality of electrical conductors may be substantially straight along the length of the conductor within the ceramic body.

The plurality of electrical conductors may include a first electrical conductor; a second electrical conductor; a third electrical conductor; a fourth electrical conductor; and/or a fifth electrical conductor.

In a second aspect of the present invention, there is provided a feedthrough including:
a ceramic body; and
a plurality of electrical conductors embedded in the ceramic body,
wherein the density of the electrical conductors exceeds 1 conductor per 300 thou$^2$ (193,584 μm$^2$) through a planar cross-section of the ceramic body, and wherein the electrical conductors have a diameter of less than 0.005 inch (127 μm).

In a third aspect of the present invention, there is provided a feedthrough including:
a monolithic ceramic body; and
a plurality of electrical conductors embedded in the ceramic body,
wherein the density of the electrical conductors exceeds 1 conductor per 300 thou$^2$ (193,584 μm$^2$) through a planar cross-section of the ceramic body, and wherein each of the plurality of electrical conductors is parallel relative to each other within 2° or each of the plurality of electrical conductors is evenly spaced apart within a tolerance of ±5% or 0.002" (50.8 μm) whichever is greater.

There is also provided a feedthrough including:
a ceramic body;
a first electrical conductor embedded in the ceramic body; and
a second electrical conductor embedded in the ceramic body,
wherein a surface of the first electrical conductor is within 0.0038 inch of a surface of the second electrical conductor.

There is also provided a feedthrough including:
a ceramic body; and
a first electrical conductor embedded in the ceramic body,
wherein the electrical conductor has a diameter of less than 0.001 inch (25.4 μm).

There is also provided a feedthrough including:
a ceramic body; and
a first electrical conductor embedded in the ceramic body,
wherein the hermeticity of the feedthrough is <1×10$^{-10}$ mbar-l/sec.

The hermeticity of the feedthrough may be <1×10$^{-11}$ mbar-l/sec.

There is also provided a feedthrough including:
a ceramic body; and
a first electrical conductor embedded in the ceramic body,
wherein the density of the ceramic body is at least 95% of the theoretical bulk density, with a standard deviation of less than 1.0% (minimum of 5 sample points taken at intervals of at least 0.002 inch apart).

Preferably, the density of the ceramic body is at least 96% or at least 97% or at least 98% or at least 98.5% of the theoretical bulk density. Preferably, the standard deviation is less than 0.5% or less than 0.4% or less than 0.3% or less than 0.2%.

There is also provided a feedthrough including:
a ceramic body;
a first electrical conductor embedded in the ceramic body; and
a second electrical conductor embedded in the ceramic body,
wherein the first electrical conductor is parallel to the second electrical conductor within 2°.

There is also provided a feedthrough including:
a ceramic body;
a first electrical conductor embedded in the ceramic body;
a second electrical conductor embedded in the ceramic body; and
a third electrical conductor embedded in the ceramic body,
wherein a distance between a surface of the first electrical conductor and a surface of the second electrical conductor is equal to a distance between a surface of the second electrical conductor and a surface of the third electrical conductor within a tolerance of ±5% or 0.002" (50.8 μm) which ever is greater.

There is also provided a feedthrough including:
a ceramic body;
a first electrical conductor embedded in the ceramic body;
a second electrical conductor embedded in the ceramic body; and a third electrical conductor embedded in the ceramic body, wherein the first electrical conductor and the second electrical conductor are in a first plane;

wherein the third electrical conductor is not within the first plane; and wherein a surface of the third electrical conductor is within 0.0038 inch of a surface of the first or second electrical conductor.

A surface of the first electrical conductor may be within 0.0038 inch (96.5 µm) of a surface of the second electrical conductor along the whole length of the first and second conductor within the ceramic matrix within a tolerance of ±5% or 0.002" (50.8 µm) which ever is greater.

The tolerance may be measured relative to the largest distance. The tolerance may be measured relative to the average distance.

The surface of each of the plurality of electrical conductors may be smooth (e.g. preferably having a mean roughness (Ra) value of less than 0.0008 inch (20.3 µm) or, more preferably, less than 0.0004 inch (10.2 µm) or, even more preferably, less than 0.0002 inch (5.1 µm) or, yet more preferably, less than 0.000125 inch (3.175 µm)). The surface of the first, second, third, fourth and/or fifth electrical conductor may be smooth.

Each of the plurality of electrical conductors may be straight or linear. The first, second, third, fourth and/or fifth electrical conductor may be straight or linear.

Each of the plurality of electrical conductors may be straight or linear along the portion within the ceramic body. The first, second, third, fourth and/or fifth electrical conductor may be straight or linear along the portion within the ceramic body.

Each of the plurality of electrical conductors may have a substantially constant cross-section. The first, second, third, fourth and/or fifth electrical conductor may have a substantially constant cross-section.

Each of the plurality of electrical conductors may have a solid cross-section. The first, second, third, fourth and/or fifth electrical conductor may have a solid cross-section.

Each of the plurality of electrical conductors may have a substantially constant cross-section along the portion within the ceramic body. The first, second, third, fourth and/or fifth electrical conductor may have a substantially constant cross-section along the portion within the ceramic body.

Each of the plurality of electrical conductors may have a solid cross-section along the portion within the ceramic body. The first, second, third, fourth and/or fifth electrical conductor may have a solid cross-section along the portion within the ceramic body.

Each of the plurality of electrical conductors may have a hollow cross-section. The first, second, third, fourth and/or fifth electrical conductor may have a hollow cross-section.

Each of the plurality of electrical conductors may have a hollow cross-section along the portion within the ceramic body. The first, second, third, fourth and/or fifth electrical conductor may have a hollow cross-section along the portion within the ceramic body.

Each of the plurality of electrical conductors may be parallel to each other within 2°. Each of the plurality of electrical conductors may be parallel to each other within 1.5°. Each of the plurality of electrical conductors may be parallel to each other within 1°. Each of the plurality of electrical conductors may be parallel to each other within 0.5°. Each of the plurality of electrical conductors may be parallel to each other within 0.2°.

The first electrical conductor may be parallel to the second electrical conductor within 2°. The first electrical conductor may be parallel to the second electrical conductor within 1.5°. The first electrical conductor may be parallel to the second electrical conductor within 1°. The first electrical conductor may be parallel to the second electrical conductor within 0.5°. The first electrical conductor may be parallel to the second electrical conductor within 0.2°.

Each of the plurality of electrical conductors may have a diameter of less than 0.0015 inch, less than 0.001 inch, or less than 0.0005 inch. The first electrical conductor may have a diameter of less than 0.0015 inch, less than 0.001 inch, or less than 0.0005 inch. The second electrical conductor may have a diameter of less than 0.0015 inch, less than 0.001 inch, or less than 0.0005 inch. The third electrical conductor may have a diameter of less than 0.0015 inch, less than 0.001 inch, or less than 0.0005 inch. The fourth electrical conductor may have a diameter of less than 0.0015 inch, less than 0.001 inch, or less than 0.0005 inch. The fifth electrical conductor may have a diameter of less than 0.0015 inch, less than 0.001 inch, or less than 0.0005 inch. Each of the plurality of conductors have a diameter of preferably at least 0.00038 inch and more preferably at least 0.0005 inch. Lower diameter conductors may be used, although at present they are not commercially available. Theoretically, conductor diameter down to at least 0.0001 may be possible given the low pressure manufacturing techniques used. Conductor diameters below these diameters may have low rigidity such that they are not self-supporting and thus are more difficult to handle in the manufacturing process.

In another embodiment, each of the plurality of electrical conductors may have a diameter of between 0.020 inch and 0.040 inch (0.508 mm to 1.02 mm). The first electrical conductor may have a diameter of between 0.020 inch and 0.040 inch (0.508 mm to 1.02 mm). The second electrical conductor may have a diameter of between 0.020 inch and 0.040 inch (0.508 mm to 1.02 mm). The third electrical conductor may have a diameter of between 0.020 inch and 0.040 inch (0.508 mm to 1.02 mm). The fourth electrical conductor may have a diameter of between 0.020 inch and 0.040 inch (0.508 mm to 1.02 mm). The fifth electrical conductor may have a diameter of between 0.020 inch and 0.040 inch (0.508 mm to 1.02 mm).

The minimum distance between the surfaces of adjacent electrical conductors, through a planar cross-section of the ceramic body, is preferably at least 0.0016 inch (40.6 µm); or at least 0.0019 inch (48.3 µm), or at least 0.002 inch (50.8 µm), or at least 0.003 inch (76.2 µm) or at least 0.004 inch (101.6 µm). Typically the distance between the surfaces of adjacent electrical conductors does not exceed 0.4 inch (10.16 mm), although greater distances are possible. In some embodiments, the distance between the surfaces of adjacent electrical conductors, through a planar cross-section of the ceramic body, is less than 0.012 inch (304.8 µm) or less than 0.006 inch (152.4 µm) or less than 0.0038 inch (96.52 µm) or less than 0.0035 inch (88.9 µm).

The feedthrough may have a thickness of less than 0.063 inch (1600.2 µm), less than 0.050 inch (1270.0 µm), less than 0.040 inch (1016.0 µm), or less than 0.030 inch (762.0 µm).

The ceramic body may have a first surface. The ceramic body may have a second surface. The first and second surfaces of the ceramic body may be parallel.

The feedthrough may have a thickness between a first surface of the ceramic body and a second surface of the ceramic body of less than 0.063 inch (1600.2 µm), less than 0.050 inch (1270.0 µm), less than 0.040 inch (1016.0 µm), or less than 0.030 inch (762.0 µm).

The cross-section of the plurality of electrical conductors may have a substantially constant cross section such that the cross section area of the conductors varies less than 10%. Preferably the cross sectional variation is less than 5% and more preferably less than 3%.

Each of the plurality of electrical conductors may extend from a first surface of the ceramic body to a second surface of the ceramic body. The first electrical conductor may extend from a first surface of the ceramic body to a second surface of the ceramic body. The second electrical conductor may extend from a first surface of the ceramic body to a second surface of the ceramic body. The third electrical conductor may extend from a first surface of the ceramic body to a second surface of the ceramic body. The fourth electrical conductor may extend from a first surface of the ceramic body to a second surface of the ceramic body. The fifth electrical conductor may extend from a first surface of the ceramic body to a second surface of the ceramic body.

The electrical resistivity, at room temperature, of each of the plurality of electrical conductors and/or the first, second, third, fourth, and/or fifth electrical conductor between the first surface of the ceramic body and the second surface of the ceramic body may be less than 4E-05 ($\Omega \cdot cm$) for Pt/Ir (90/10).

Preferably, the electrical resistivity, at room temperature, of each of the plurality of electrical conductors and/or the first, second, third, fourth, and/or fifth electrical conductor between the first surface of a green ceramic body (i.e. before sintering) and the second surface of the green ceramic body may be less than 70% or less than 60%, more preferably less than 50% or less than 40%, even more preferably less than 30% or less than 25%; and yet even more preferably less than 20% compared to the electrical conductors embedded into the ceramic body (i.e. after sintering).

The density of the ceramic body is preferably at least 95% of the theoretical bulk density, more preferably at least 96% or at least 97%, even more preferably at least 98% or at least 98.5%; and yet even more preferably at least 99%. The standard deviation of the density (minimum of 5 samples and preferably a minimum of 7 samples) is preferably less than 1.0%, more preferably less than 0.5% and even more preferably less than 0.2%.

Each of the plurality of electrical conductors may be discrete from each other. The first, second, third, fourth and/or fifth electrical conductors may be discrete from each other.

Each of the plurality of electrical conductors may be electrically isolated from each other. The first, second, third, fourth and/or fifth electrical conductors may be electrically isolated from each other.

A distance between a surface of each of the plurality of electrical conductors and a surface of another of the electrical conductors may be equal within a tolerance of ±5% (preferably ±4%, more preferably ±3%), or 0.002" (50.8 µm) whichever is greater. The tolerance may be measured relative to the largest distance. The tolerance may be measured relative to the average distance.

The plurality of electrical conductors may include at least three conductors, at least four conductors, at least five conductors, at least six conductors, at least seven conductors, at least eight conductors, at least nine conductors, at least ten conductors, at least 11 conductors, at least 12 conductors, at least 13 conductors, at least 14 conductors, at least 15 conductors, at least 16 conductors, at least 17 conductors, at least 18 conductors, at least 19 conductors, at least 20 conductors, at least 24 conductors, at least 25 conductors, at least 30 conductors, at least 35 conductors, at least 40 conductors, at least 45 conductors, at least 48 conductors, at least 50 conductors, at least 55 conductors, at least 60 conductors, at least 65 conductors, at least 70 conductors, at least 72 conductors, at least 75 conductors, at least 80 conductors, at least 85 conductors, at least 90 conductors, at least 95 conductors, at least 92 conductors, at least 100 conductors, at least 120 conductors, at least 144 conductors, at least 168 conductors, at least 192 conductors, at least 216 conductors, at least 240 conductors, at least 264 conductors, at least 288 conductors, at least 312 conductors, at least 336 conductors, or at least 360 conductors, or at least 720 conductors, at least 780 conductors, at least 840 conductors, at least 900 conductors, at least 960 conductors, at least 1020 conductors, at least 1080 conductors, at least 1440 conductors and at least 1800 conductors and at least 2160 conductors.

The properties of the first, second, third, fourth and/or fifth conductors and the relationships between the first, second, third, fourth and/or fifth conductors may also be features of some or all or the plurality of conductors (e.g. three of the plurality of conductors, four of the plurality of conductors, five of the plurality of conductors).

The second, third, fourth and/or fifth electrical conductor may have any or all of the properties and/or relationships with the first electrical conductor described above.

The third, fourth and/or fifth electrical conductor may have any or all of the properties and/or relationships with the first and/or second electrical conductors described above.

The feedthrough may comprise additional electrical conductors. The additional electrical conductors may have any or all of the properties and/or relationships with the other electrical conductors described above.

The feedthrough may comprise a second, third, fourth and/or fifth plurality of electrical conductors. The second, third, fourth and/or fifth plurality of electrical conductors may have any of the features described above in relation to the plurality of conductors.

The feedthrough may be implantable within a human or animal body. The feedthrough may be biocompatible. Biocompatible materials are compatible with living tissue. Biocompatible materials do not produce a toxic or immunological response when exposed to the body or bodily fluids.

The feedthrough may further include a flange or ferrule.

The flange or ferrule may be of or include titanium, niobium, tantalum, diamond, stainless steel, aluminium, copper, nickel, tungsten, platinum or alloy thereof.

The flange or ferrule may be hermetically bonded to the ceramic.

The feedthrough may be bonded to a titanium alloy flange or ferrule by use of a non-gold containing braze alloy such that the transus temperature of the titanium alloy is not exceeded.

The feedthroughs described above may advantageously be included in devices.

Accordingly, there is also provided a device, e.g. a medical device, including the feedthroughs described above.

A shell of the medical device may be bonded to the ceramic of the feedthrough.

A shell of the medical device may be bonded to the flange or ferrule of the feedthrough (when present).

The shell may be of or include titanium or a titanium alloy.

The feedthrough may be hermetically bonded to the medical device.

The feedthrough may be bonded to a titanium alloy shell of the medical device by a use of a non-gold containing braze alloy such that the transus temperature of the titanium alloy is not exceeded.

Green bodies for co-firing to form the feedthroughs described above are also provided.

Accordingly, there is also provided a green body for co-firing to form a feedthrough including:
   a green ceramic body; and
   a plurality of electrical conductors embedded in the ceramic body,
   wherein the density of the electrical conductors exceeds 1 conductor per 23 thou$^2$ (14,839 μm$^2$) through a planar cross-section of the green ceramic body.

There is also provided a green body for co-firing to form a feedthrough including a plurality of electrical conductors embedded in a green ceramic body, in which the plurality of elongate electrical conductors traverse the green ceramic body in a non-coplanar relationship.

Methods for forming the feedthroughs and green bodies are also provided.

Accordingly, there is provided a method of forming an assembly of electrical conductors at least in part embedded in a ceramic or a ceramic precursor matrix, the method including the steps of:
   a) mounting a plurality of elongate electrical conductors to a frame to form a conductor-frame assembly including a plurality of elongate electrical conductors;
   b) introducing a fluid ceramic or ceramic precursor into a cavity to form a self-supporting body,
wherein the self-supporting body embeds at least part of the elongate electrical conductors.

Mounting the plurality of elongate electrical conductors to the frame preferably includes fixedly attaching the plurality of elongate electrical conductors to the frame.

This method is able to produce a monolithic ceramic structure in which the embedded electrical conductors are not subject to forces capable of significantly deforming the conductors from their original framed position. This contrasts to layered ceramic structures in which the electrical conductors are subject to excessive pressures (e.g. greater than 2 atmosphere (absolute)) in their formation, resulting in distortion of the electrical conductors.

Consequently, the method enables the production of ceramic structures having a combination of small conductor diameters, small minimum distance between the surfaces of adjacent electrical conductors, small conductor-to-conductor center-to-centre spacings, and high conductor density.

There is also provided use of a fluid ceramic or ceramic precursor in the manufacture of a feedthrough, wherein the fluid ceramic or fluid ceramic precursor is introduced into a cavity at a pressure of less than 2 atmosphere (absolute) to form a self-supporting ceramic body. The conductor-frame assembly preferably traverses the cavity prior to the introduction of the fluid ceramic or ceramic precursor.

In some embodiments, the conductor-frame assembly is positioned into the self-supporting body (i.e. after the fluid ceramic or ceramic precursor has been introduced into the cavity). Within this embodiment, the elongate electrical conductors are preferably mounted at one end to the frame, such that the frame is not embedded into the self-supporting body. Low viscosity (e.g. 0.05 to 10.0 Pa·s and preferably 0.1 to 5.0 Pa·s at a strain rate of 1 sec$^{-1}$) ceramic fluid or ceramic precursor fluid (i.e. not pastes) are preferred to avoid distortion/misalignment of the conductors upon entry in the fluid. The solids loading of the ceramic fluid or ceramic precursor may be in the range of 10 to 80 volume %, depending upon the solid characteristics. More preferably, the solids loading is in the range of 20 to 60 volume %.

To minimise tolerances in spacing between the conductors, it is preferably that each end of the elongate electrical conductors are mounted to the frame. Preferably, the elongate electrical conductors are free from intermediate supports between each of the ends of the elongate electrical conductors. Although, in some embodiments in which the rigidity of the elongate electrical conductors are not sufficient to be self-supporting, intermediate supports may be used. The intermediate supports are preferably a green ceramic and more preferably of the same composition of the self-supporting body.

The term "elongate electrical conductors" includes, without limitation, wires, strips, pins, rods, tubes and bars of conductive material.

"Traverses a cavity" is meant to mean extending across or through at least part of the cavity and should not be read as limited to extending across the entire extent of the cavity. "Traverse" should be read in like manner.

"Fluid ceramic or ceramic precursor" should be read as meaning a fluid including ceramic or ceramic precursor. "Ceramic precursor" means a material that while not necessarily a ceramic itself, can be converted to a ceramic by appropriate processing. By fluid is meant capable of flowing under the applicable processing conditions and includes, without limitation, fine particulates, slurries, slips, suspensions, solutions, pastes, and mixtures thereof.

"Self-supporting body" means a body that does not collapse on removal of the frame.

The cavity may have a periphery defined in part at least by the frame.

The method may further include removing part at least of the frame.

The plurality of elongate electrical conductors may traverse the cavity in a coplanar relationship, lying in a single plane.

The plurality of elongate electrical conductors may traverse the cavity in a non-coplanar relationship.

The plurality of elongate electrical conductors may include at least one planar array of elongate electrical conductors defining a plane, and at least one elongate electrical conductor non-parallel with said plane.

The plurality of elongate electrical conductors may traverse the cavity in at least two groups of elongate electrical conductors, the conductors in each group being in a coplanar relationship to define a group plane.

The group planes of at least two of the plurality of groups may be non-parallel.

The plurality of elongate electrical conductors may comprise at least one group of elongate electrical conductors diverging from a first region of the cavity periphery to a second region of the cavity periphery, the first region being smaller in area than the second region.

The cavity may include one or more walls extending from a base, and at least one of said plurality of elongate electrical conductors may be mounted to traverse the cavity from the base to said one or more walls.

At least two of said plurality of elongate electrical conductors may be mounted non-parallelly to traverse the cavity from the base to said one or more walls The frame may include a plurality of frame parts assembled to form the frame.

The method may further include the steps:
   d) mounting each of a first group of elongate electrical conductors by ends thereof to a first group of frame parts e) securing a second group of frame parts in fixed relationship to the first group of frame parts f) mounting each of a second group of elongate electrical conductors by one end to the second group of frame parts, and by another end to either one of the first or second group of frame parts.

The steps d) e) f) may be repeated, with further groups of frame parts being successively mounted to the groups of frame parts, and each conductor of successive groups of elongate electrical conductors being mounted by one end to the further group of frame parts, and by another end to frame parts of the further group or to frame parts of previously mounted groups.

One or more of the groups of frame parts may be or include a single frame part.

One or more elongate electrical conductors may be mounted by one end to a frame part, and by another end to an electronic component disposed in the cavity to be embedded in the ceramic.

The elongate electrical conductors are preferably fixedly attached to the frame. Any suitable attachment means may be used including, but not limited to, diffusion bonding; mechanical fastening; adhesive (e.g. UV curable resin); laser assisted diffusion bonding; and welding (e.g. laser welding, brazing, and/or soldering).

Mounting a plurality of elongate electrical conductors to the frame preferably includes welding to join the elongate electrical conductors to metallic regions of the frame.

The frame is preferably more rigid than the elongate electrical conductors, which it supports. The frame is preferably sufficiently rigid that the frame maintains its form during the introduction of the fluid ceramic or precursor thereof to embed the conductors.

The frame may be metallic and the metallic regions of the frame may include surface portions of the frame.

The frame may be non-conductive and the metallic regions of the frame may include metallic inserts in the frame.

The elongate electrical conductors may include nickel, molybdenum, tantalum, tungsten or an alloy thereof. Additionally or alternatively, the elongate electrical conductors be include Pt, Ir, Nb, Pd, Au, Os, Ni, Cr, W, Mo, Ta, Fe, Co, Ti, Rh, Re, Zr, V and their alloys may also be used for the conductors.

The elongate electrical conductor may include a platinum group metal or alloy. In embodiments, with narrow diameter conductors (e.g. <0.002 inch (50.8 µm)), platinum alloys (e.g. 5 wt % Ir/95 wt % Pt) or conductors with at the same rigidity as 5 wt % Ir/95 wt % Pt or greater, are preferred to increase positional stability during manufacture. More rigid conductors also enable longer feedthrough lengths to be fixedly attached to a frame during manufacturing.

The metallic regions of the frame may include an iron alloy. For example, an iron nickel alloy. The iron nickel alloy may include from 30 wt % to 40 wt % nickel and/or from 60 wt % to 70 wt % iron, e.g. 36% Ni+Fe. Additionally or alternatively, Fe, Ni, Pd, Pt, Co, Cr, Al, Cu, Mo, Ta, W and their alloys may also be used.

The body may be formed in the cavity as a green ceramic body which is fired to co-sinter the ceramic on to the elongate electrical conductors to provide a hermetic join between ceramic and elongate electrical conductors.

There is also provided a feedthrough comprising a plurality of elongate electrical conductors embedded in a ceramic body and obtainable by the described method.

There is also provided a feedthrough comprising a plurality of elongate electrical conductors embedded in a ceramic body and obtained by the described method.

Features described in relation to the feedthrough or the assembly of electrical conductors or the methods may be features of the feedthrough or the assembly of electrical conductors or the methods even though not necessarily expressly enumerated as such mutatis mutandis.

The terms inch(es) and " may be interchangeable used throughout the specification.

The term "diameter" is inclusive of effective diameter (average of the width at the narrowest diameter and the largest diameter).

The term "thou" equates 0.001 inches. The term $thou^2$ equates to 0.000001 $inches^2$ or square inches.

Further aspects of the present disclosure will be evident from the claims and from the following specific description.

BRIEF DESCRIPTION OF THE DRAWINGS

Embodiments will now be described by way of example only with reference to the accompanying drawings, in which:

FIGS. 3(a), (b), and (c) show SEM micrographs of a platinum—Fe—Ni invar joint at respectively 170×, 1,200× and 12,000× magnifications;

FIGS. 6(a) and (b) show respectively, a plurality of frame parts with elongate electrical conductors mounted thereto prior to forming a ceramic body to embed part at least of the elongate electrical conductors; and the resultant pattern of conductors embedded in the (not shown) ceramic;

FIGS. 6(c) and (d) show respectively, sectional views of a plurality of frame parts with elongate electrical conductors mounted thereto prior to forming a ceramic body to embed part at least of the elongate electrical conductors; and a sectional view of the resultant pattern of conductors embedded in the (not shown) ceramic;

FIGS. 16(*a*), (*b*) and (*c*) show SEM micrographs of a cut section of a prior art feedthrough;

FIGS. 17(*a*), (*b*) and (*c*) show SEM micrographs of a cut section of a feedthrough;

DESCRIPTION OF EMBODIMENTS

General Description of Process

The present disclosure provides methods of forming an assembly of electrical conductors at least in part embedded in a ceramic or a ceramic precursor matrix, the method including the steps of:
a) mounting a plurality of elongate electrical conductors to a frame to form a conductor-frame assembly including a plurality of elongate electrical conductors traversing a cavity;
b) introducing a fluid ceramic or ceramic precursor into the cavity to form a self-supporting body embedding part at least of the elongate electrical conductors.

Figure 1:
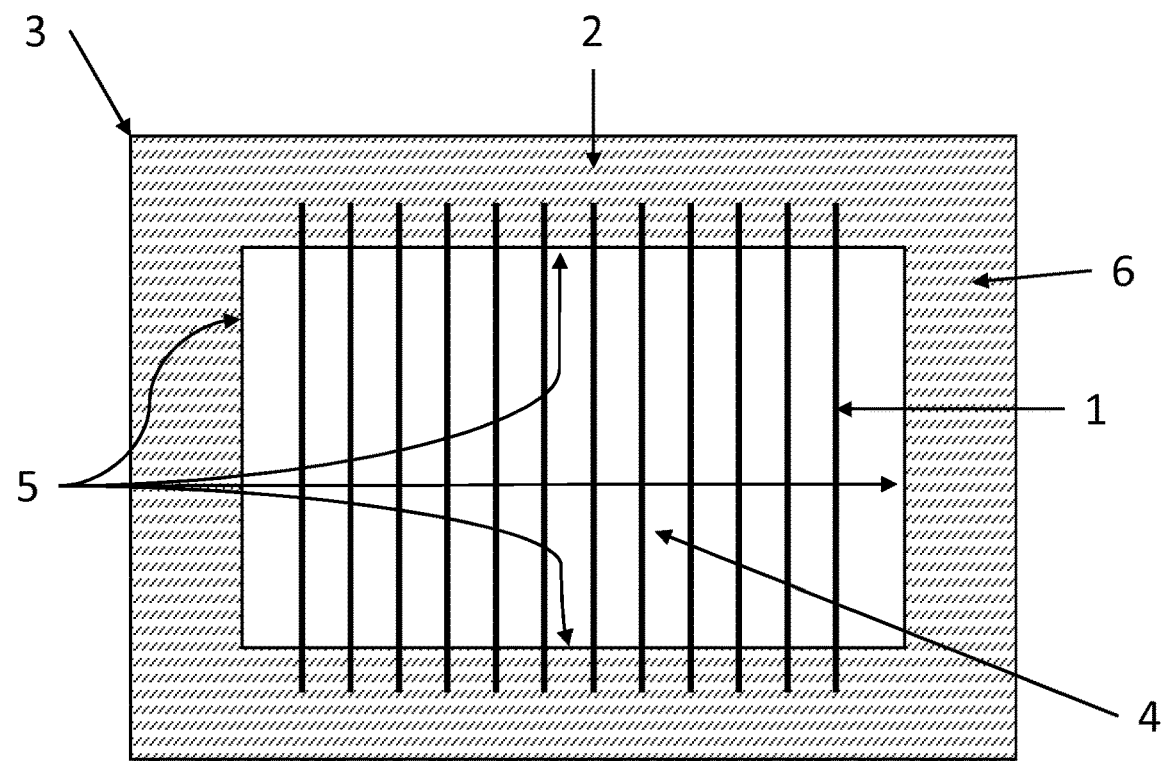
FIG. 1 shows schematically a plurality of elongate electrical conductors mounted to a lead frame.

FIG. 1 shows schematically a plurality of elongate electrical conductors 1 mounted to a lead frame 2 to form a conductor-frame assembly 3. The elongate electrical conductors 1 extend within a cavity 4 defined by walls 5 of the lead frame 2. The elongate electrical conductors 1 can be mounted or fixedly attached to the lead frame by any convenient means (e.g. adhesively, by brazing, welding or otherwise).

Figure 2:
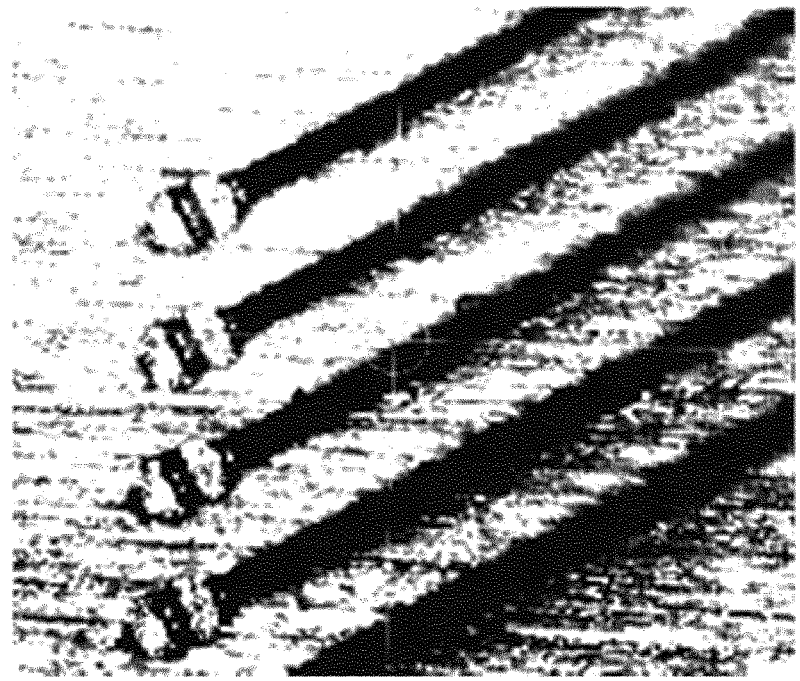
FIG. 2 shows a picture of platinum wires bonded onto a Fe—Ni lead frame.

FIG. 2 shows a picture of platinum wires bonded onto a Fe—Ni lead frame and FIGS. 3(*a*), (*b*), and (*c*) show details of such bonds. Details of why such a combination may be advantageous are presented below under the heading "The conductors and frame".

For a feedthrough including a single layer of conductors, the conductor-frame assembly may be mounted in a die and the ceramic formed around the elongate electrical conductors 1 in the cavity 4. The fluid ceramic or ceramic precursor may be introduced through an aperture in the die, or through an optional aperture 6 formed in the lead frame 2, or both.

For feedthroughs including two or more layers of conductors the conductor-frame assemblies 3 may be stacked.

Figure 4:
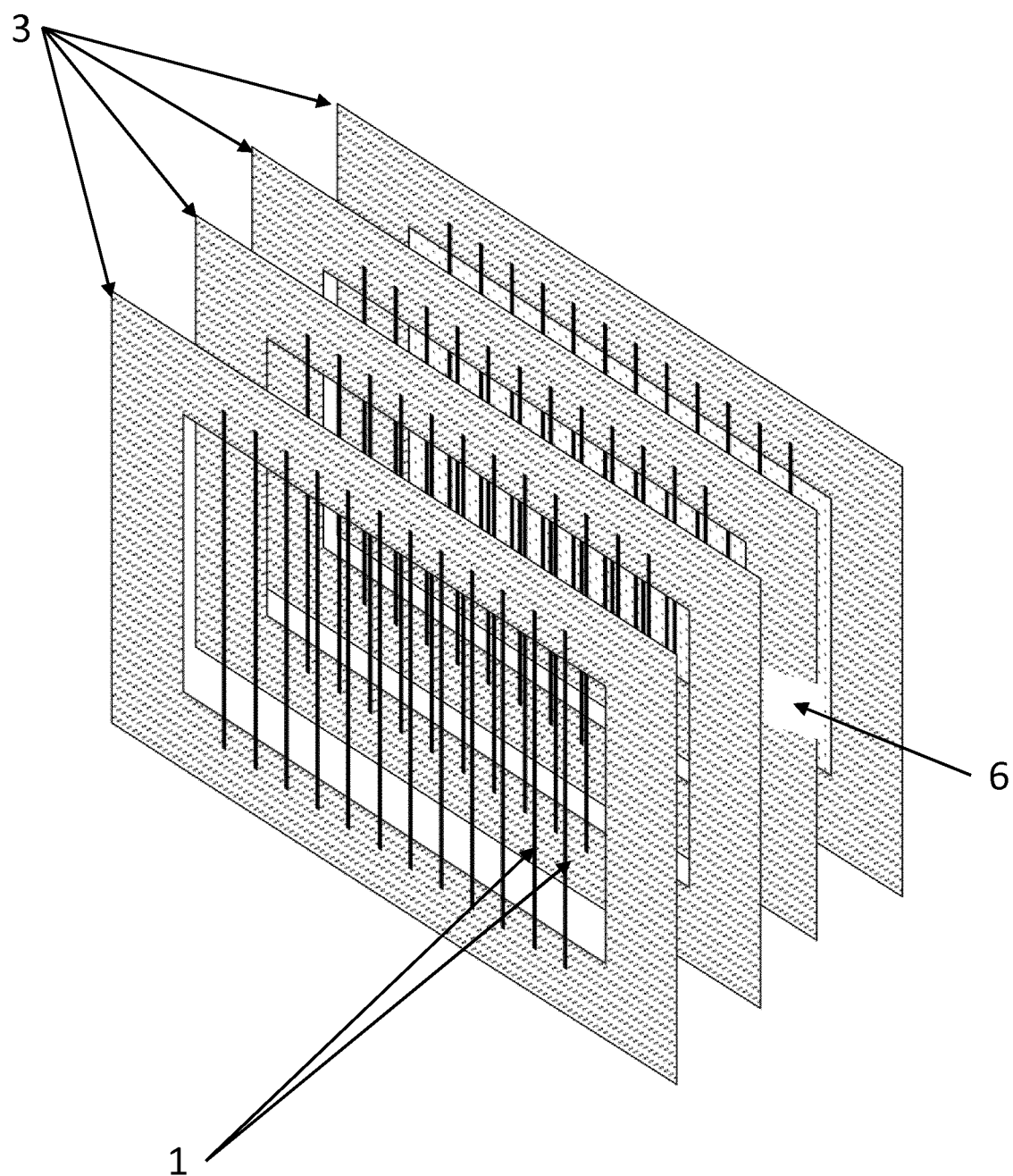
FIG. 4 shows schematically a plurality of the lead frames of FIG. 1 stacked prior to forming a ceramic body to embed part at least of the elongate electrical conductors.

FIG. 4 shows several conductor-frame assemblies 3 stacked adjacently to form a conductor frame so that the elongate electrical conductors 1 form a multi-layered array of elongate electrical conductors 1. Subsequent forming of a ceramic body embedding part at least of the elongate electrical conductors 1 creates an assembled ceramic body having embedded parallel elongate electrical conductors 1. The assembled ceramic body can undergo processing while in the frame (which is removed subsequently), and/or after removal of the frame.

For example the ceramic body may be a green ceramic body that is subsequently fired to sinter and densify the ceramic as described below.

As shown the separate conductor-frame assemblies 3 are shown stacked in a parallel relationship. This is not essential, particularly if it is desired that the conductors diverge from a first region on one face of the ceramic body to a second region of the ceramic body, the first region being smaller in area than the second region.

Processing of the assembled ceramic body can include (without limitation) steps of drying, curing, sintering, annealing, or melting or a combination of two or more such steps, dependent on the nature of the ceramic used. Details of particular ceramics are presented below under the heading "The ceramic".

Processing of the assembled ceramic body can also include (without limitation) slicing the assembled ceramic body to form feedthroughs, polishing, exterior grinding (e.g. OD grinding, profile grinding), slicing, polishing (if required), metalization of surfaces that will be brazed, brazing, testing (e.g. hermeticity testing). Of course, other subsequent processing steps known to the skilled person may also be employed.

A particularly useful process is to co-sinter a green ceramic body to form a monolithic dense ceramic body around the conductor. Co-sintering of metals like platinum (e.g. platinum group metals [Pt, Ir, Os, Pd, Rh, Ru] or alloys thereof) with oxide/non-oxide ceramics has been shown to occur without any surface deterioration of the metal phase provided that appropriate (e.g. non-oxidising) atmospheres are used during sintering to inhibit metal degradation.

Studies have shown that certain refractory metals (e.g. platinum, molybdenum, nickel, tungsten, and their alloys) do not react (e.g. oxidize, nitride) appreciably when co-sintered with oxide and/or non-oxide ceramics. Such reactions can inhibit the performance (e.g. electrical conductivity and hermeticity) of the feedthrough, making these metals particularly suitable for use in feedthroughs. Further, the sintering stresses from the ceramic matrix during the densification process causes the polycrystalline matrix to shrink and press on to the plastic surface of platinum or other refractory metal at the ceramic sintering temperatures (1050° C. to 1800° C.). This mechanical stress assures a strong mechanical bond between the metal and the ceramic matrix. When the composite is sintered to full density, it assures that the bond between the metal/alloy conductor and the ceramic matrix is hermetic. By "full density" it is meant a density of more than 90%, more than 94%, more than 98% or more than 99% theoretical density.

The present disclosure is not limited to co-sintering but this technique is particularly useful.

Figure 5:
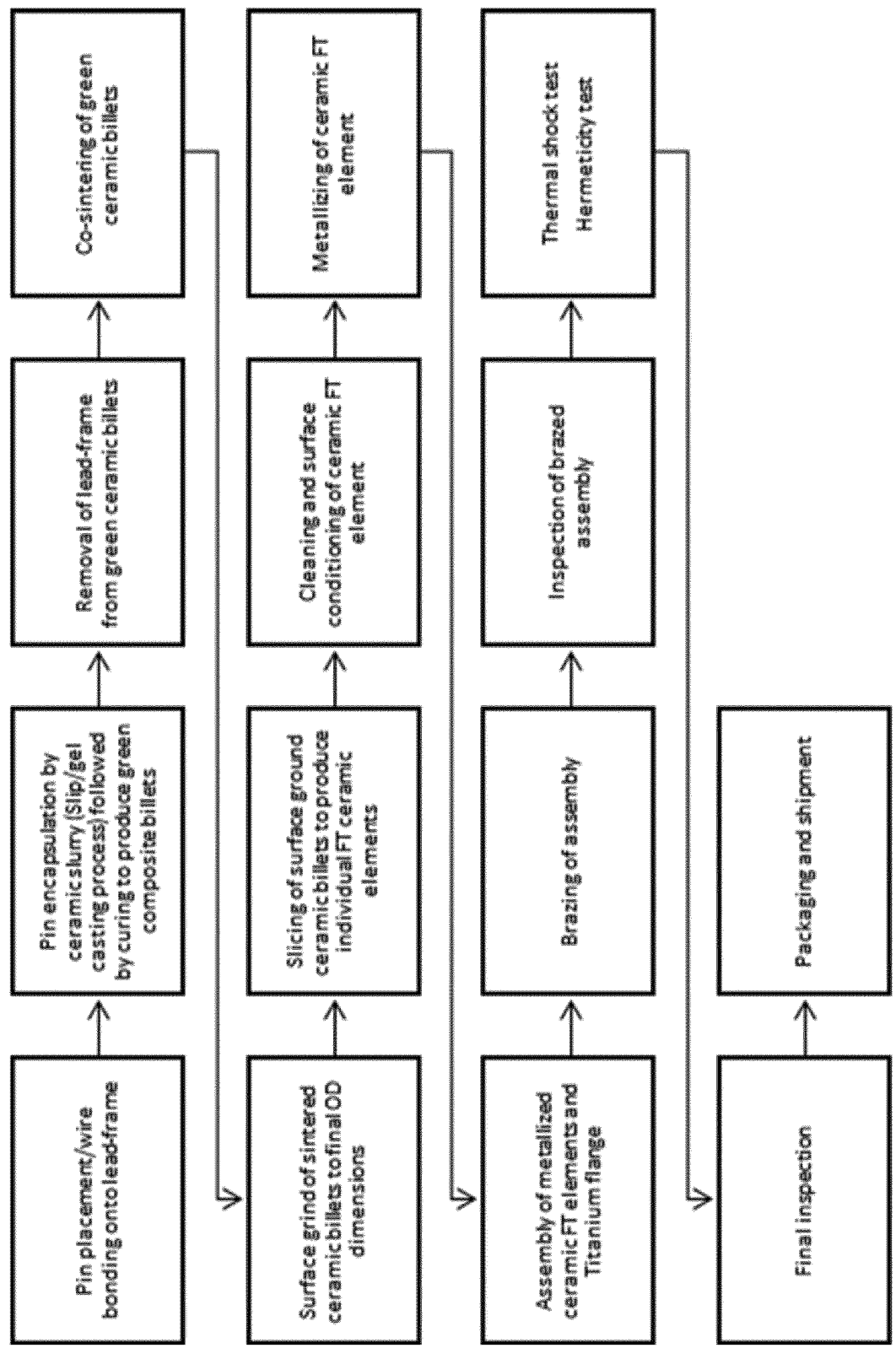
FIG. 5 shows a generalised process diagram showing steps in a method of forming assemblies of electrical conductors at least in part embedded in a ceramic matrix.

The process exemplified in FIGS. 1-4 can result in feedthroughs in which the conductors are generally disposed in layers, albeit with a small inter-conductor separation than the prior art [see Example 1 below]. The general process conforms to the flow diagram of FIG. 5 setting out a generalised process.

Figure 7:
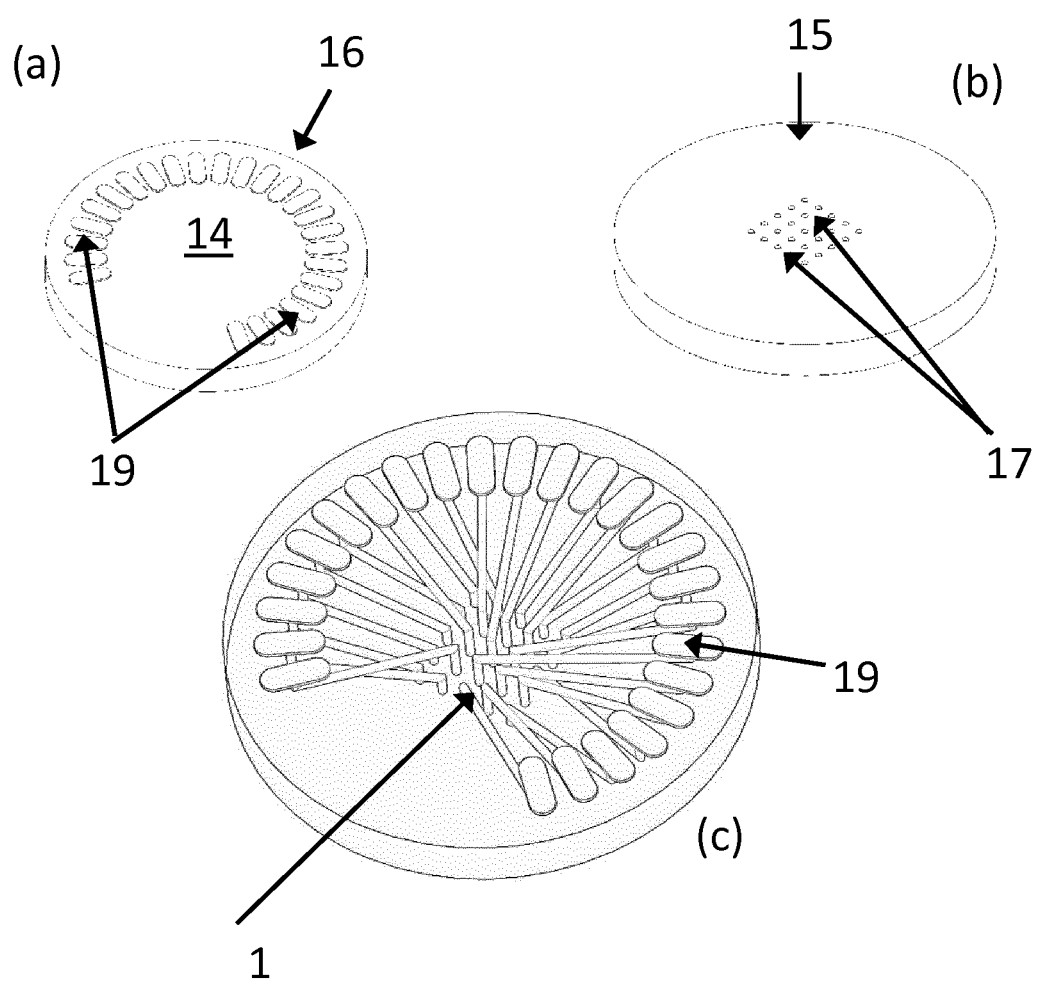
FIGS. 7(a), (b), and (c) show respectively top view, bottom view, and sectional view of a feedthrough.

FIGS. 6 and 7 show an approach that permits more complex conductor geometries to be achieved in which the elongate electrical conductors are in a non-layered relationship.

In FIGS. 6(*a*) and 6(*c*) elongate electrical conductors 1 are bonded at one end in a predefined pattern to a base plate/ring and the other ends are bonded to subsequent stacked lead frame parts/rings. The conductors are subsequently encapsulated in a self-supporting ceramic or ceramic precursor body yielding the 3D conductor architecture shown in FIGS. 6(b) and 6(d) in which elongate electrical conductors 1 diverge from a base plane 7 to a number of positions displaced from the base plane 7.

FIG. 6(c) shows a typical process in more detail than FIG. 6(a).

In this process, first conductors 7 are each mounted by one end to a base plate 8 and by their other ends to a first frame layer 9.

Second frame layer 10 is then stacked over first frame layer 9 and second conductors 11 mounted in like manner to both base plate 8 and second frame layer 10.

The second conductors 11 may be mounted to the base plate 8 radially and/or rotationally displaced from the first conductors 7 to provide a desired separation; or may be mounted coincidentally with the first conductors 7, where a common connection is intended to be provided to the first conductors 7 and second conductors 11. The process is repeated with successive stacking of frame layers until a desired height is reached.

The frame layers may be stacked directly on each other or with spacers lying between the frame layers. Further details of the frame layers may be found below under "The conductors and frame". As will be apparent to the skilled person, the frame may be stacked in a horizontal or a vertical fashion depending upon the design of the feedthrough desired.

After forming the self-supporting ceramic or ceramic precursor body, the frame parts are removed to leave a ceramic body 12 (FIG. 6(d)) including embedded electrical conductors. Removal of the frame parts may be mechanical (e.g. grinding away) or chemical (e.g. dissolution) or both, as appropriate for the materials used. Dependent on how mounted to the frame, the elongate electrical conductors may leave protruding parts 13, which can be useful in some applications.

In FIG. 7 a feedthrough 14 is shown including a first face 14 and opposed second face 15. Elongate electrical conductors 1 diverge to form a non-collinear and non-coplanar 3D array. The elongate electrical conductors 1 diverge from a narrowly spaced 2D array 17 on the second face 15 to widely spaced 2D array 18 on first face 16 where they are terminated at contacts 19.

Figure 8:
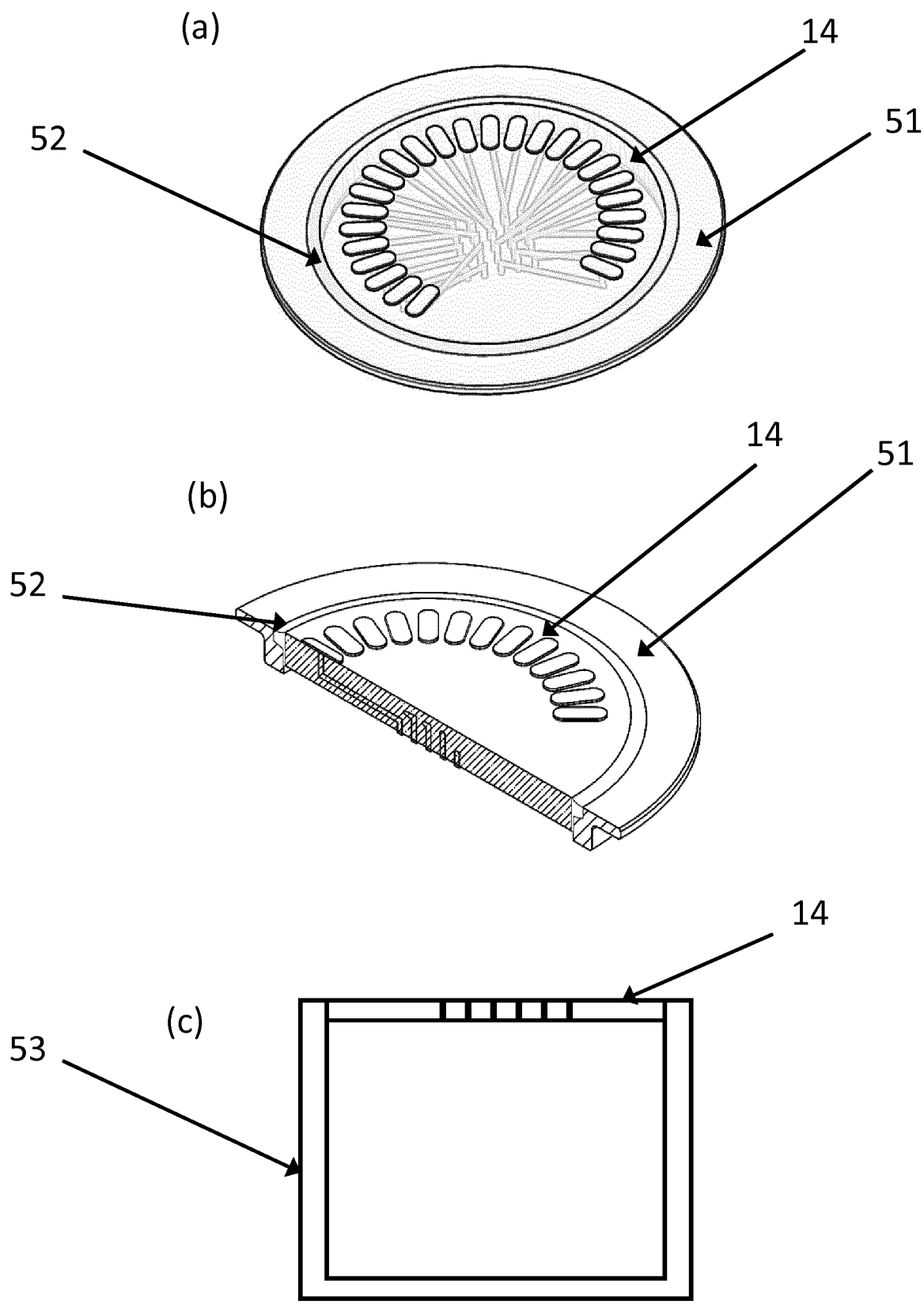
FIGS. 8(a) and (b) show respectively top view and sectional view of the feedthrough of FIG. 7 further including a flange.
FIG. 8(c) schematically illustrates the feedthrough included in a device

In FIGS. 8(a) and (b) the feedthrough 14 of FIG. 7 is shown mounted in a flange or ferrule 51. The feedthrough 14 is shown mounted to the flange or ferrule 51 with a brazed join 52. However, any alternative join may be used. For example, the attachment of the feedthrough to a device may be made using the techniques described in U.S. Pat. Nos. 8,103,433 and/or 9,351,436, which are hereby incorporated by reference.

FIG. 8(c) schematically illustrates the feedthrough 14 included in a device 53. As illustrated, a flange or ferrule is not used to attach the feedthrough 14 to the device 53. However, a flange or ferrule may be used, depending upon the design of the device 53.

Figure 9:
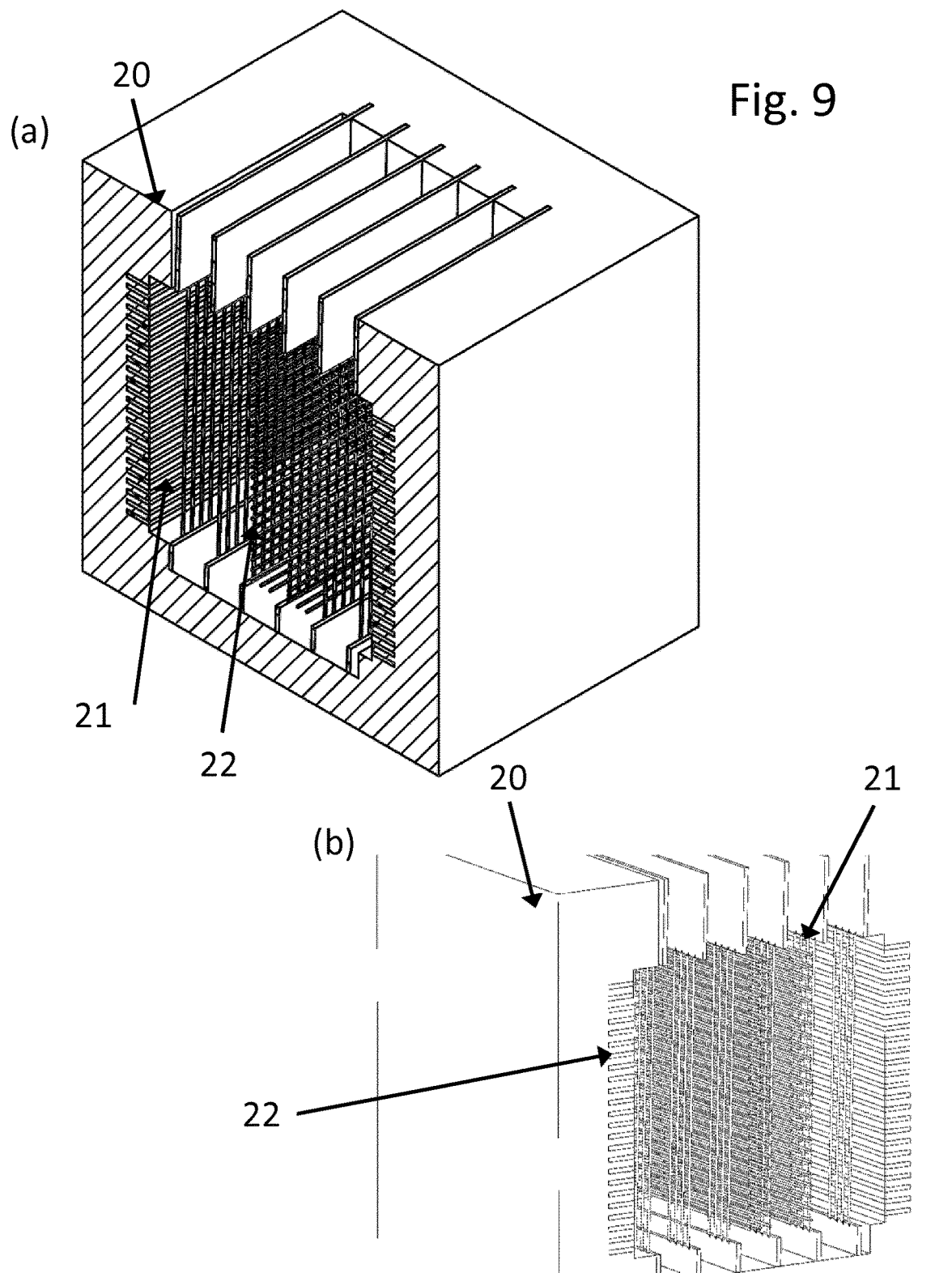
FIGS. 9(a) and (b) show schematically a further feedthrough.

FIGS. 9(a) and (b) show a feedthrough 20 including two groups of elongate electrical conductors, the conductors in a first conductor group 21 being in a coplanar relationship defining a first group plane, and the conductors in a second conductor group 22 being in a coplanar relationship defining a second group plane. The conductors in first conductor group 21 are in parallel relationship to each other. The conductors in second conductor group 22 are also in a parallel relationship to each other. However, the conductors may be divergent within their respective group plane.

The first group plane 21 includes 24 conductors. There are 14 further group planes parallel to the first group plane 21. The second group plane 22 includes 10 conductors. There are 5 further group planes parallel to the second group plane.

It should be noted that the examples shown above are by no means the only geometries that can be produced. Many complex shapes can be envisioned that can be produced by the technique of mounting the conductors to a frame and embedding the conductors in ceramic prior to removing the frame. These shapes include geometries like hemispherical shaped curved contacts and hollowed 3D shapes and many more.

Further, individual ceramic bodies including embedded conductors may themselves be joined to form still more complex arrangements.

Figure 13:
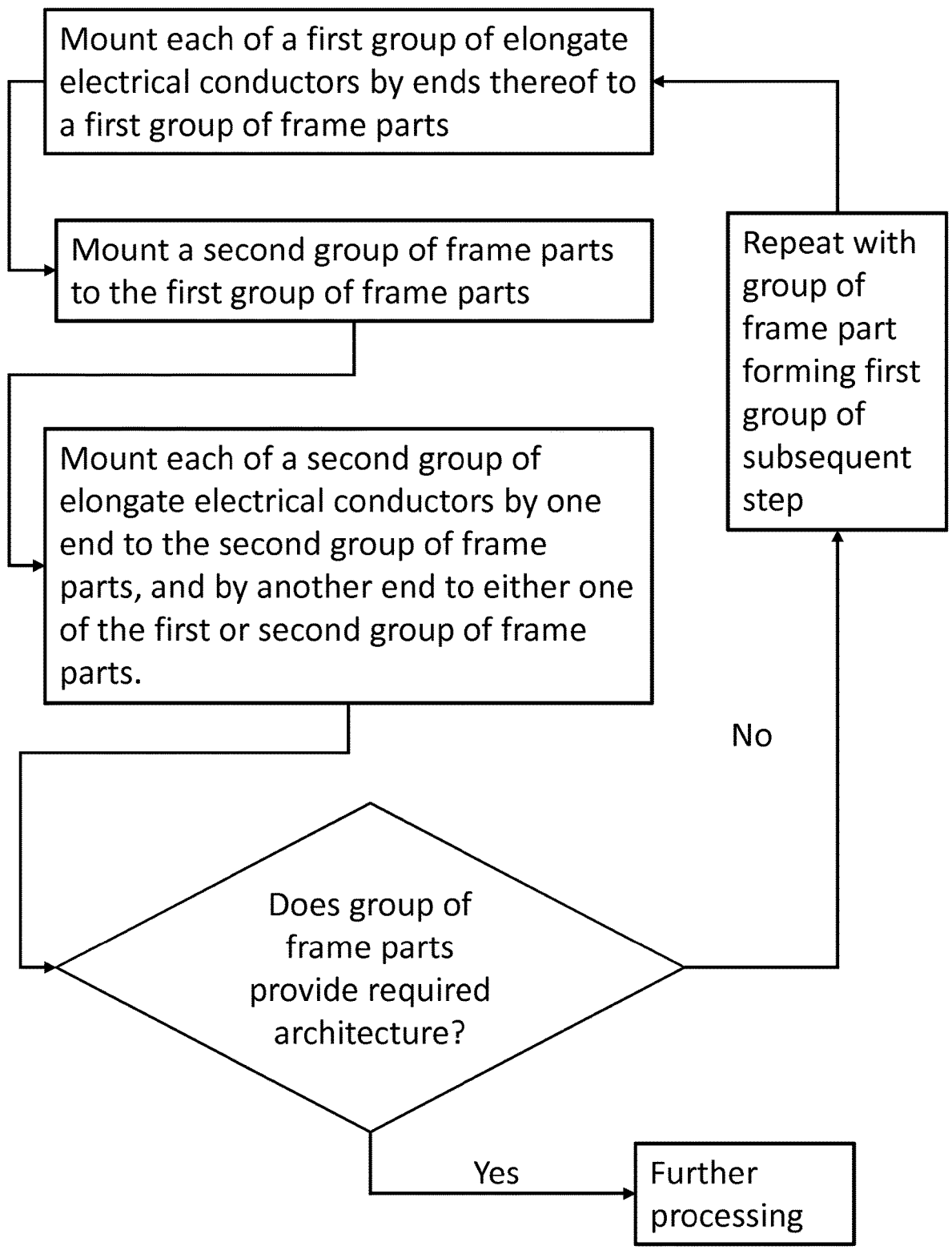
FIG. 13 shows schematically a method of assembling a conductor-frame assembly prior to further processing.

FIG. 13 shows schematically a process for producing a conductor-frame assembly. This process includes
a) mounting each of a first group of elongate electrical conductors by ends thereof to a first group of frame parts
b) mounting a second group of frame parts to the first group of frame parts
c) mounting each of a second group of elongate electrical conductors by one end to the second group of frame parts, and by another end to either one of the first or second group of frame parts.

If the groups of frame parts with elongate electrical conductors provides a desired architecture, then the group of frame parts is passed on to further processing. If not, then the process is repeated with the product of one cycle forming the first frame group of the next cycle. During this process, optionally, electronic components can be mounted to the frame for embedding in the ceramic.

The Conductors and Frame

Dependent upon application, the elongate electrical conductors may be of any suitable material, but particularly useful materials for use when co-sintering of the ceramic is required, are inert or refractory metals like platinum, niobium, iridium, nickel, etc. or alloys which are a combination of those. Platinum and 10% Ir/Pt have been used in the examples below. Accordingly, Pt or 0-15% Ir/Pt or 0-10% Ir/Pt or 8-12% Ir/Pt may be used to form the conductors. Pt, Ir, Nb, Pd, Au, Ni, Cr, W, Mo, Ta, Fe, Co, Ti, Rh, Re, Zr, V and their alloys may also be used for the conductors.

Further, if use of a non-precious metal can enable the frame to be produced economically.

A wide range of metals and alloys can form solid solutions with platinum.

To this end the Invar family of alloys, Fe—X (X=Ni, Pd and Pt) have been considered to be successful candidates for lead frame material. Fe—Ni alloys were chosen for the examples below, in particular 36% Ni+Fe, as they are inexpensive compared to the other two in the Invar family. However, Fe, Ni, Pd, Pt, Co, Cr, Al, Cu, Mo, Ta, W and their alloys may also be used.

FIG. 2 shows Pt wires welded to a Fe—Ni frame. FIGS. 3(a), (b), and (c) show scanning electron micrographs of the Pt-Invar interface at magnifications of 170×, 1200× and 12000× respectively, showing a good bond.

The conductor and frame dimensions are selected to meet the application. Typical conductor diameters are 0.00038 inch or 0.001 inch to 0.040 inch. For example, 0.0005 inch, 0.001 inch, 0.002 inch, 0.005 inch, 0.010 inch, 0.020 inch, 0.030 inch, or 0.040 inch. Typical conductor ranges include any of these values, for example, 0.0005 inch to 0.005 inch, 0.0005 inch to 0.002 inch, 0.0005 inch to 0.001 inch, 0.001 inch to 0.002 inch.

Frame parts to which the elongate conductors are mounted, and spacers between adjacent frame parts, may include recesses to accommodate parts of the conductors lying between adjacent frame parts.

Figure 14:
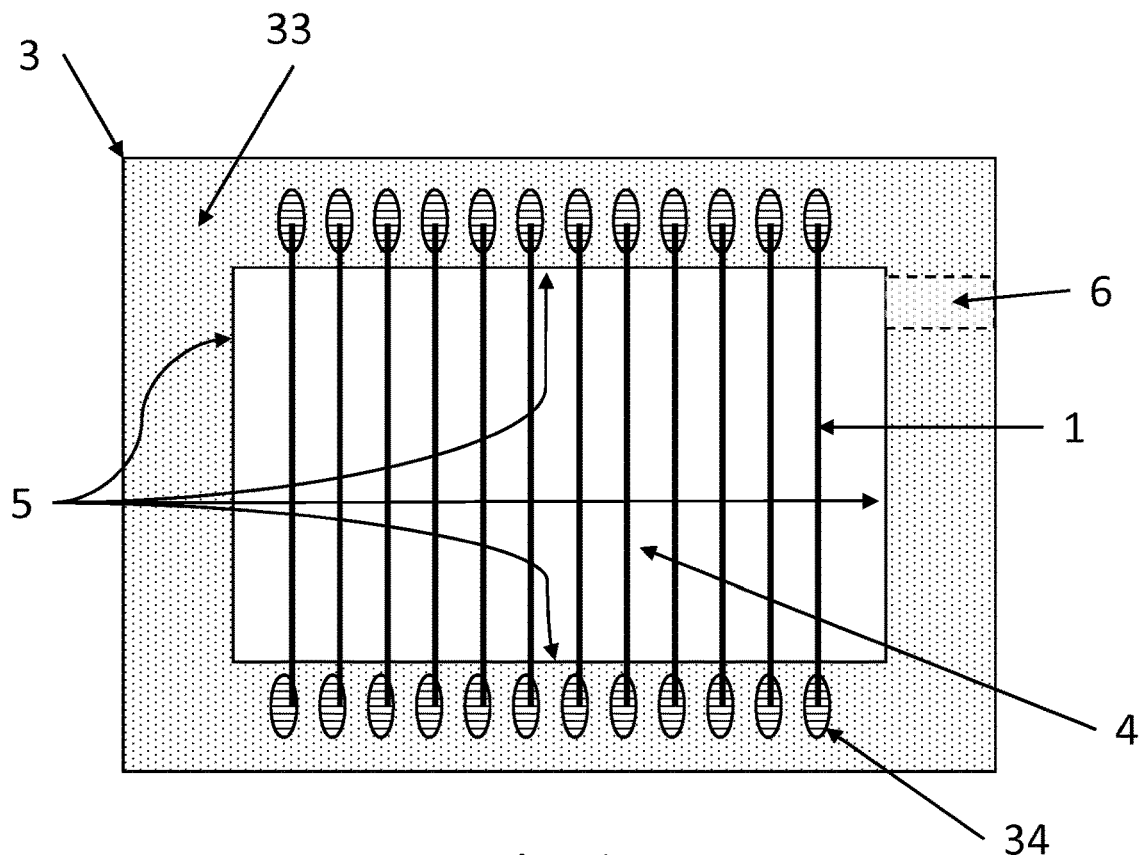
FIG. 14 shows schematically a plurality of elongate electrical conductors mounted to an alternative lead frame to that shown in FIG. 1.

The frame and frame parts may each include a single body of material to which the conductors are bonded, or a composite body including regions of material to which the conductors may be bonded, and regions of material not capable of being bonded to the conductors. FIG. 14 shows conductor-frame assembly 3 similar to that of FIG. 1, but in which a non-conductive lead frame 33 carries metallic pads 34, which may be either surface mounted or embedded in the non-conductive lead frame 33, and in which the elongate conductors are mounted to the metallic pads 34.

Figure 15:
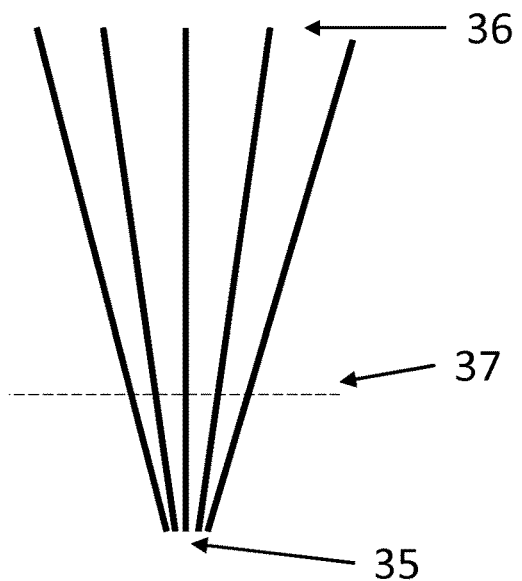
FIG. 15 shows schematically an arrangement of conductors extending from a closely mounted region to a widely mounted region.

It should be noted that precision mounting of the wires to the frame may on occasion be difficult where a very narrow conductor-conductor separation is required. In some circumstances this can be dealt with by positioning the conductors to the frame closer than the desired conductor spacing and then machining to expose the conductors at the desired conductor spacing. FIG. 15 shows conductors 1 mounted to a frame in a closely mounted region 35, and further apart in a widely mounted region 36 and then, after forming the ceramic body, removing the surface of the body to expose a plane of desired conductor spacing 37.

As will be appreciated, after the method has been completed it may be possible to re-use part or all of the frame.

Solid conductors having a circular cross-section may be used. In particular as such conductors are available as wire, they may be economic. The avoidance of angular geometries (e.g. ellipsoidal) also mitigates the risks of crack formation during the co-sintering process. However, other cross-sectional shapes may be used. For example, hollow conductors may be used in the method to provide feedthroughs having hollow conductors.

The Ceramic

Any oxide, non-oxide or mixed oxide-non-oxide may be used as required for the application. Typical ceramics and composites include, but are not limited to, BN, $B_4C$, $Si_3N_4$, TiC, TiN, TaN, $Al_2O_3$, ZrO2, $SiO_2$, MgO, ZnO, CaO, BeO, MnO, $Y_2O_3$, $Nb_2O_5$, $Cr_2O_3$, $SnO_2$, $MnO_2$, TaO, CuZO, BeO, NiO and other lanthanide oxides or a combination, of two or more of these in the form of a compound like spinel or glass ceramics like Macor® or a solid solution.

The present disclosure also contemplates the use of glasses and glass ceramics. However, for certain applications use of a non-glass based ceramic may be desirable. For example, certain glasses may react with human or animal bodily fluids reducing the biostability of the feedthrough. Therefore, non-glassed based ceramics may be chosen in order to increase biostability of the formed feedthrough.

The ceramic can be formed around the elongate electrical conductors by any suitable process giving the degree of bonding and hermeticity required by the intended application.

Typical processes include, slip casting, gel casting, low pressure-low viscosity thermoplastic injection moulding, fluidized bed direct transfer, low stress casting, zero pressure casting, casting by gravity feed, casting without application of external pressure, and other alternatives that will be apparent to the skilled person. Preferably, the processes do not expose the elongate electrical conductors to significant pressure, which may lead to distortion and misalignment. Preferably, the processes are performed at less than 2 atmosphere (absolute), more preferably less than 1.8 atmosphere (absolute) or less than 1.5 atmosphere (absolute); and even more preferably under ambient atmosphere (i.e. 1.0 atmosphere (absolute)) and even more preferably under vacuum. Conventional powder injection moulding of ceramic is typically operated at pressures in the 10 s or 100 s of atmosphere and are thus unsuitable for the production of feedthroughs under the scope of the present invention.

Desirable features to achieve high density and hermeticity in a composite body are:

void free casting stress free green body homogeneous green density throughout the green body A co-sintering process may be used to densify a green body in which the ceramic matrix encapsulates the metal pin array. The selection of the co-sintering process parameters are dependent on the metal-ceramic system chosen. Typically, the temperature can range from 1050° C. to 1800° C. for the peak sintering temperatures. The environment can also change from air atmosphere to inert to other atmosphere or vacuum. In some cases, if a binder is used the green monoliths can be run through an air oven for binder burn-out and subsequently transferred to a high temperature furnace for sintering. In some cases, pressure assisted sintering may also be used.

Example 1

Figure 10:
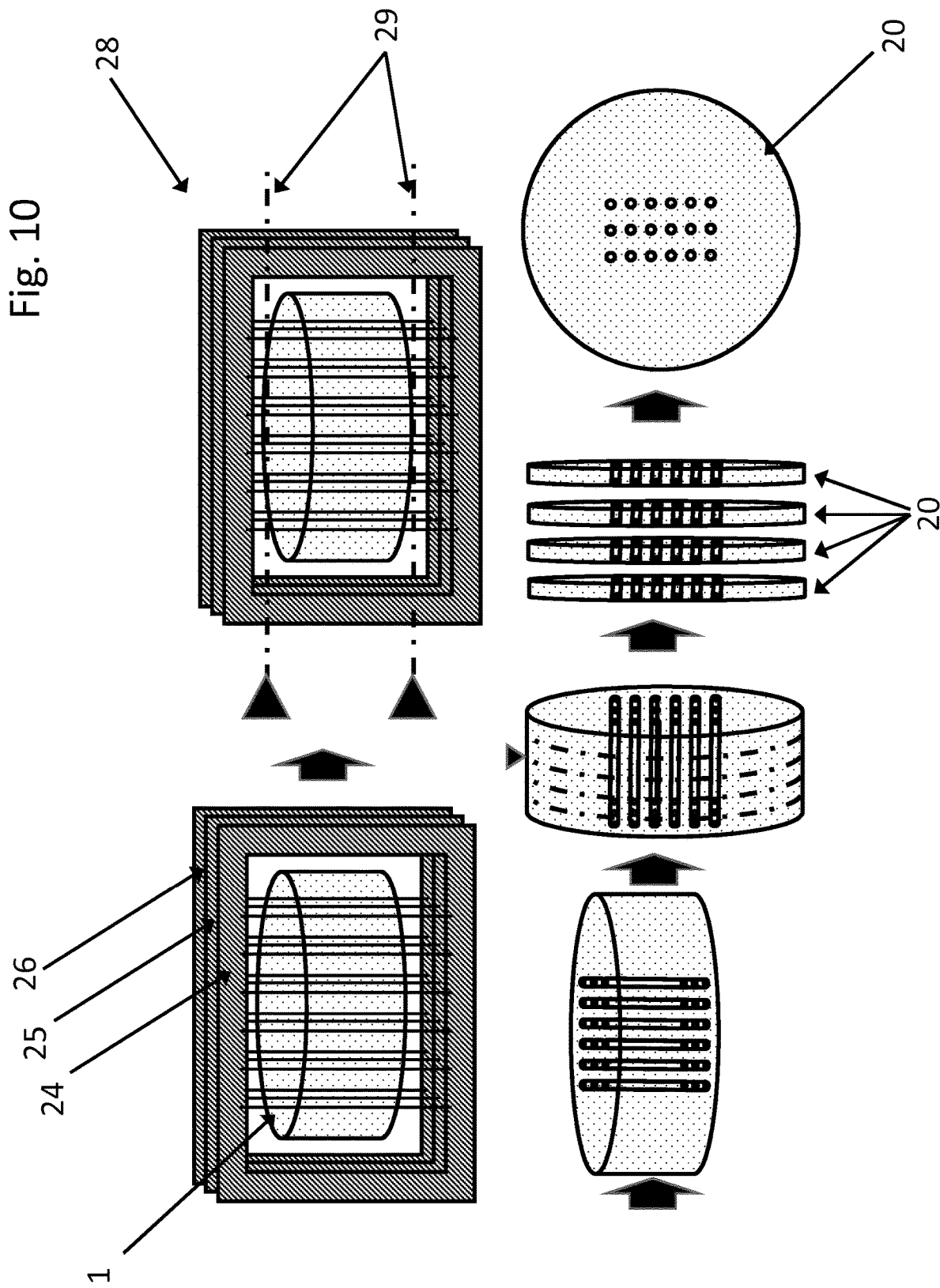
FIG. 10 shows schematically the manufacture of a feedthrough made in accordance with the present disclosure.

Alumina was used as the insulating ceramic and platinum wires were used as the electrical conductors. The electrical conductors formed conductive vias in the feedthrough. FIG. 10 shows the overall process up to and including embedding the elongate electrical conductors 1 in ceramic.

Platinum wires 1 were bonded to a conductor-frame assembly precursors 24, 25, 26 using the wire bonding process. The individual lead frames 25, 26, 27 were then arranged into the desired pattern to form an assembly 28 of lead frames 25, 26, 27. The assembly 28 was then placed in a mould/die (indicated schematically at 29) and followed by the casting of the ceramic matrix using a gel-casting approach.

Gel casting of alumina was accomplished as follows: A 99.9% pure alumina slurry was made with acrylic dispersant and water followed by the addition of a monomer methacrylamide and cross-linker polyethyleneglycoldimethylacrylate. The solids loading of the alumina was about 40 vol. %

Alternative gel casting approaches may be used, as will be apparent to the skilled person. Gel casting methods which produce zirconia ceramics, zirconia toughened alumina (ZTA) ceramics, yttria-tetragonal zirconia polycrystal (3Y-TZP) alumina ceramics, and/or other ceramics may be used. For example, those described in publications U.S. Pat. Nos. 5,028,362 and/or 6,066,279 may be used.

After co-firing, the individual feedthroughs 20 are subsequently diced out of the co-fired monolith or in other cases may be over-moulded individually based on the design.

This process permits extremely thin (<400 μm) insulator plates to be made with integral conductors running therethrough in a closely spaced (<250 μm spacing) relationship.

Example Densities

The table below shows the density distribution of the ceramic matrix using a forming system with samples taken at intervals of at least 0.002 inch (50 μm) apart. As seen a >98% density was achieved with a very low standard deviation.

| Density (Alumina matrix) | |
| --- | --- |
| Sample | Example 1 |
| #1 | 3.905 |
| #2 | 3.913 |
| #3 | 3.903 |
| #4 | 3.91 |
| #5 | 3.912 |
| #6 | 3.913 |
| #7 | 3.912 |
| Average | 3.909714286 |
| StDev. | 0.004070802 |
| Avg. RD | 98.98% |
| StDev RD | 0.10% |

Figure 23:
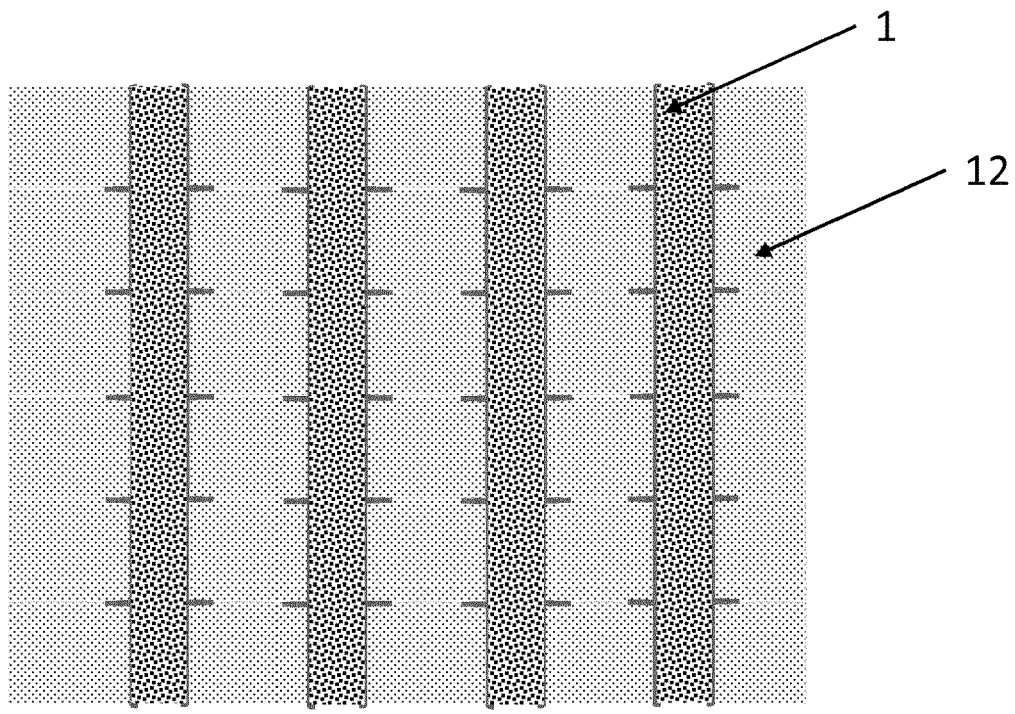
FIG. 23 shows schematically the density of a feedthrough constructed according to a prior art method.
Figure 24:
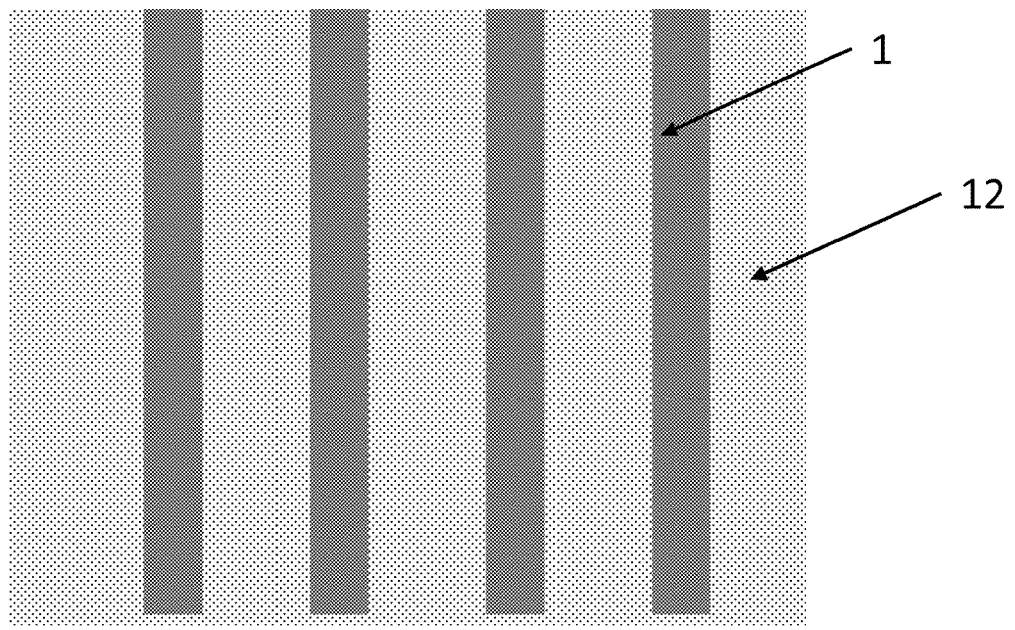
FIG. 24 shows schematically the density of a feedthrough.

It is understood that the good theoretical densities are achieved because of the low porosity resulting from the method of formation employed. With reference to FIGS. 23 and 24, in a ceramic laminate prior art (see FIG. 23) around conductors 1 within a ceramic body 12 as the conductors 1 are not uniform and protrude into the ceramic 12, areas of greater porosity and lower density can form. However, when the feedthrough is made in accordance with the present disclosure (see FIG. 24), as the conductors are uniform, with constant cross-section, there are no/fewer areas of reduced density and increased porosity.

As the density of the ceramic around the conductors is more uniform, there are fewer stress risers within the ceramic. In turn, fewer stress risers can result in increased hermeticity and/or maintenance of a high degree of hermeticity over an extended period of time. Further, as fewer stress risers are present greater miniaturisation is possible, as a feedthrough of a smaller size can have sufficient integrity.

A known alternative to the ceramic laminate of FIG. 23 is the use of a platinum ink which has similar problems to a ceramic laminate.

Example SEM Images

Figure 11:
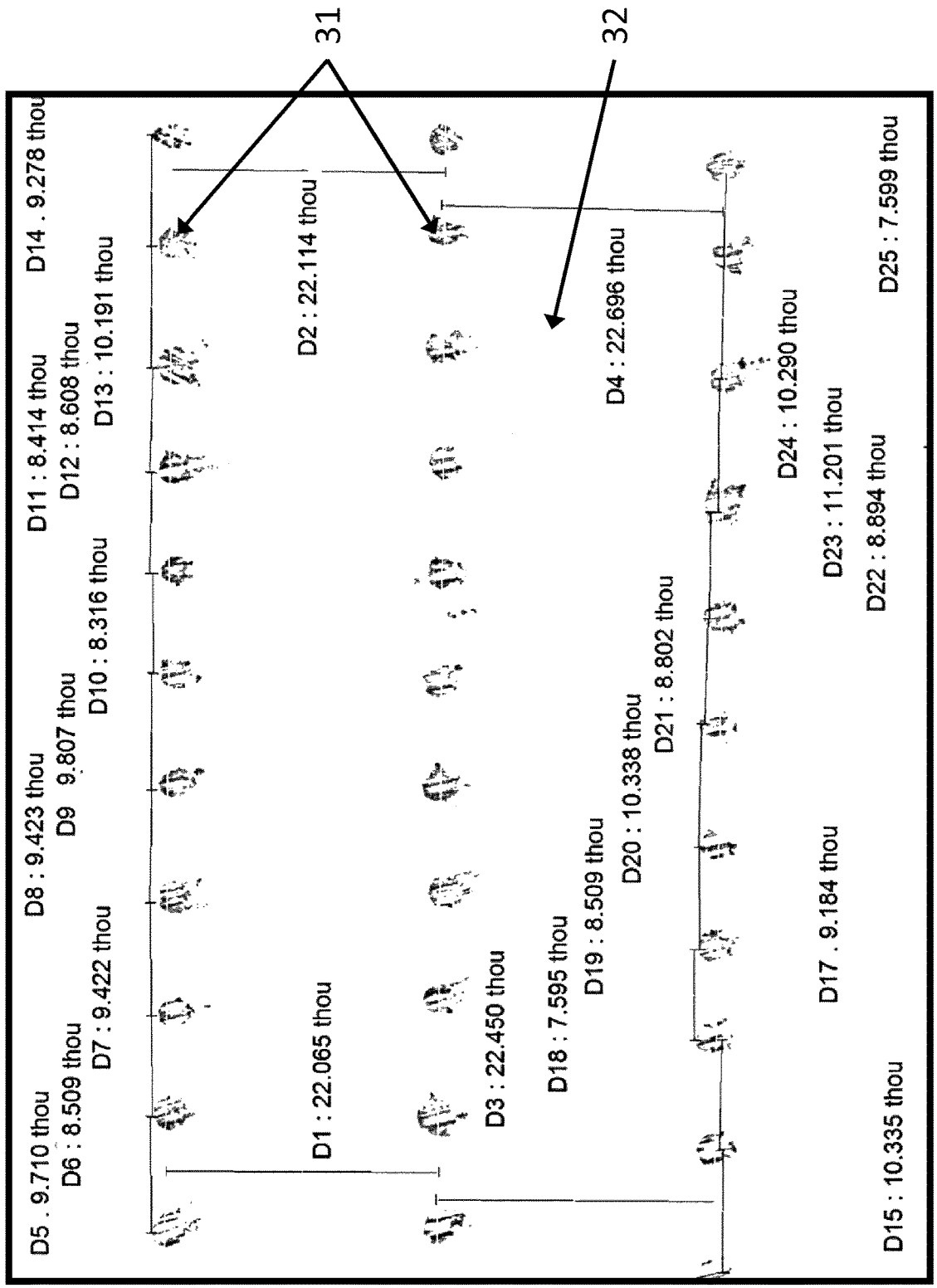
FIG. 11 is a micrograph of a cut section of a feedthrough.

FIG. 11 shows a cut section of a high density feedthrough made by this process, using 50 μm [≅0.002 inch] diameter platinum conductors 31 embedded in a monolithic alumina matrix 32. The conductors are arranged in layers, and shown are measurements made of conductor positions. This figure shows that the process of the present disclosure is readily able to achieve a conductor to conductor pitch within a layer of approximately 250 μm [9.22 thou ≅234 μm] with a standard deviation of less than 25 μm [0.962 thou ≅24.4 μm]. The separation between layers of conductors was approximately 570 μm [average 22.33 ≅567 μm] with a standard deviation of less than 10 μm [0.2973 thou ≅7.6 μm]. Interlayer spacing is determined by the lead frame thickness and any spacing between lead frames, and this example is not optimised for close spacing.

Figure 12:
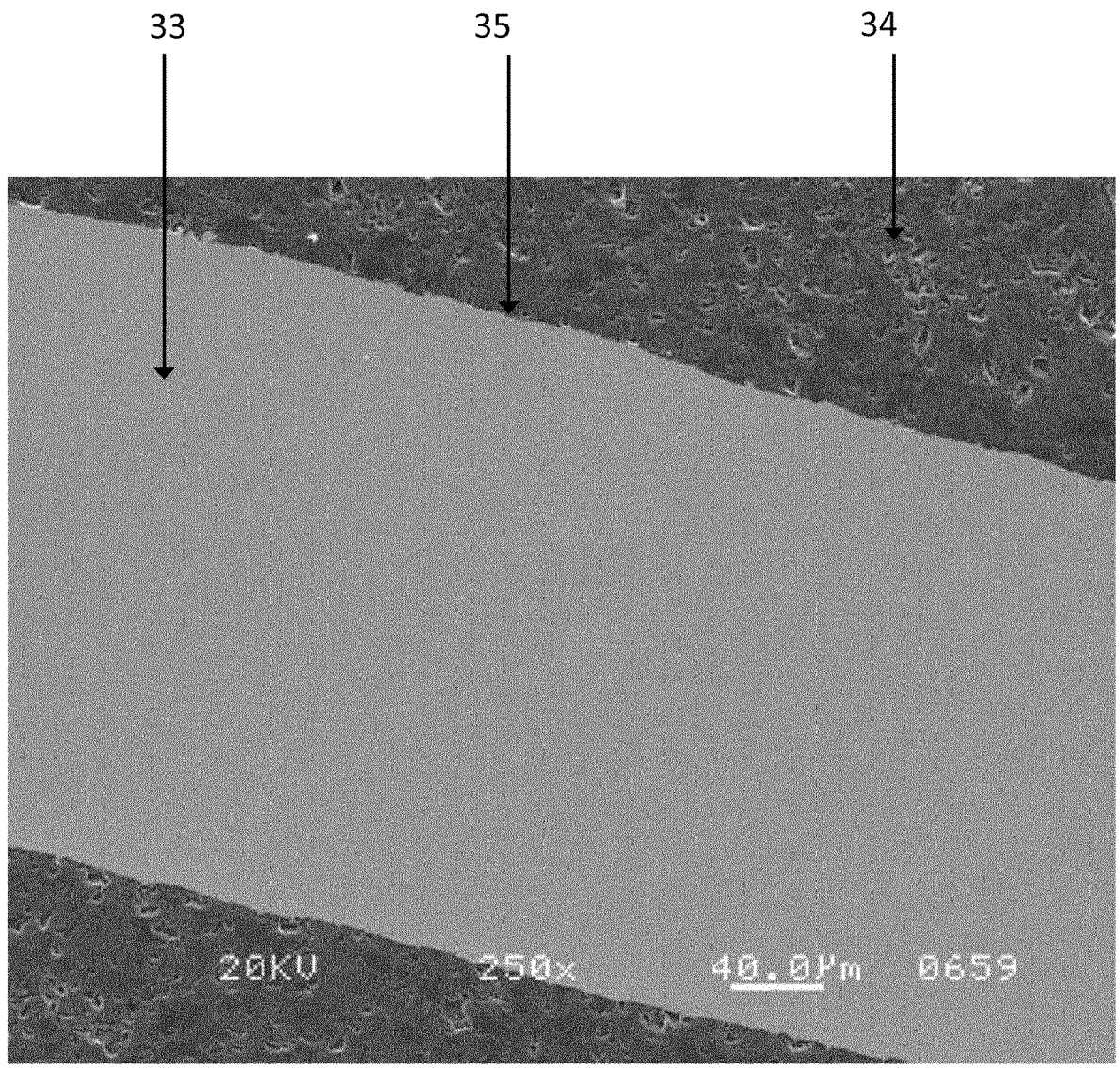
FIG. 12 shows a polished cross section of a platinum pin embedded in alumina.

FIG. 12 shows that the phase boundary 35 between the platinum and the alumina matrix is clean, showing no signs of chemical diffusion or metal deterioration.

Example Conductor Uniformities

FIG. 16 shows a prior art feedthrough including a metallic conductor within a ceramic matrix. In this case, the feedthrough was prepared according to the method of U.S. Pat. No. 8,698,006. FIGS. 16(a), 16(b) and 16(c) show images wherein the surface of the conductor has been polished to differing depths. As is apparent, the surface shown is in the plane of the conductor.

The conductor is approximately 0.002 inch (50 μm) in diameter. Whilst using the method of U.S. Pat. No. 8,698,006 it was desired to achieve a conductor having a uniform cross-section, however, it can be seen that the cross-section is not uniform as the edges of the conductor are jagged or have a zigzag profile. It is therefore apparent that the conductors do not have a smooth or uniform surface. As shown in FIG. 16, the deviation due to slip/distortion can be up to 25 μm for a 50 μm pin.

FIG. 17. shows a feedthrough including a metallic conductor within a ceramic matrix prepared using the present method. When observing these SEM images it should be noted that the ceramic matrix (ZTA) is very hard. It is therefore difficult to polish a perfect interface between the ceramic and the Pt pin. The visible porosity and scrub-offs are artefacts of the polishing process and not features of the feedthrough. Nevertheless, it is clear that the wires are not zig-zagged.

Further, it can be seen that the conductors are parallel within 1°. The deviation shown is exaggerated here due to polishing artefacts. There is no gross slip observed in the pin. (The same deviation is also present in the previous process (FIG. 16), however, it is overshadowed by the gross slip deviations.)

Figure 18:
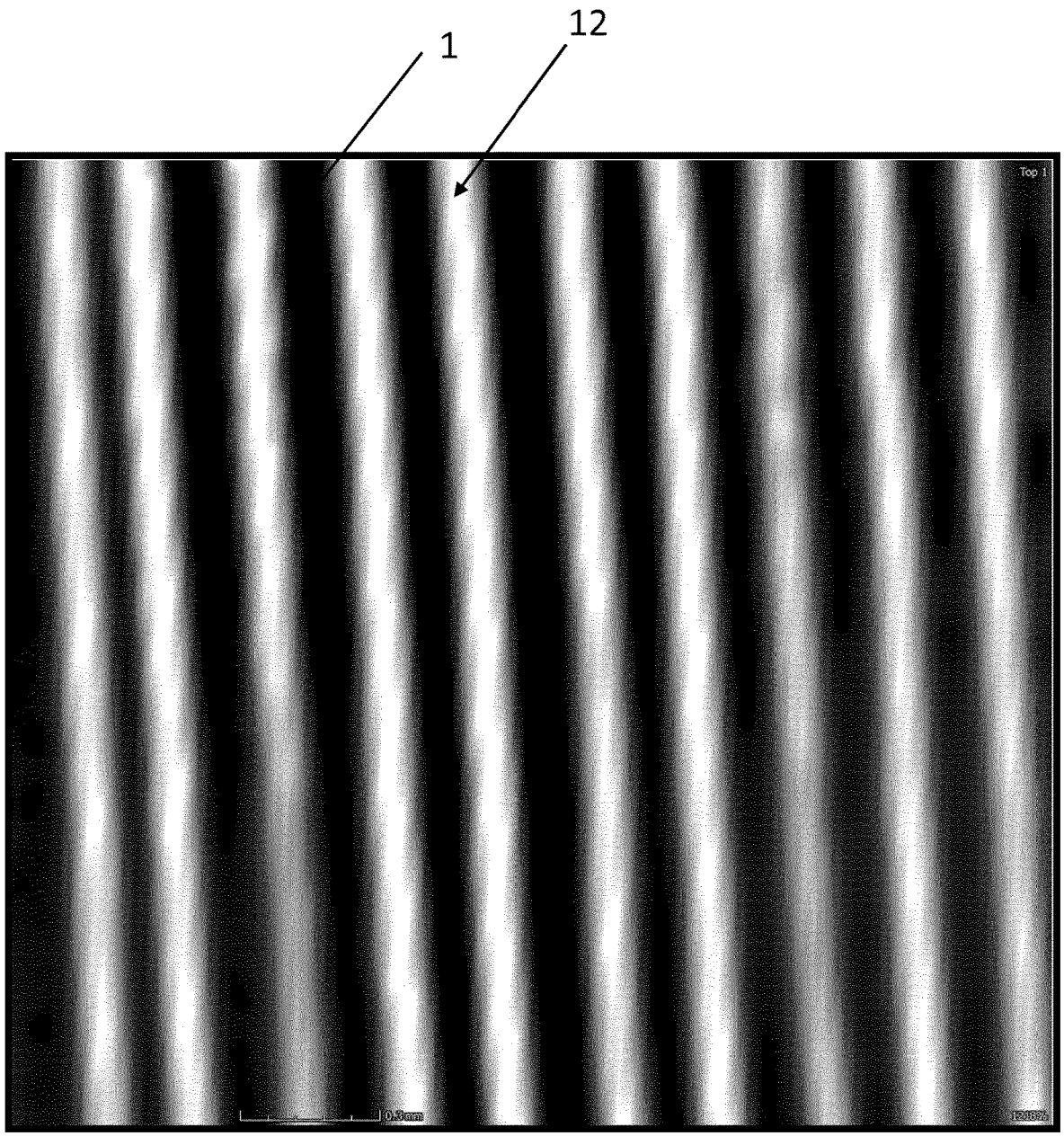
FIG. 18 shows an X-ray image of a feedthrough.
Figure 19:
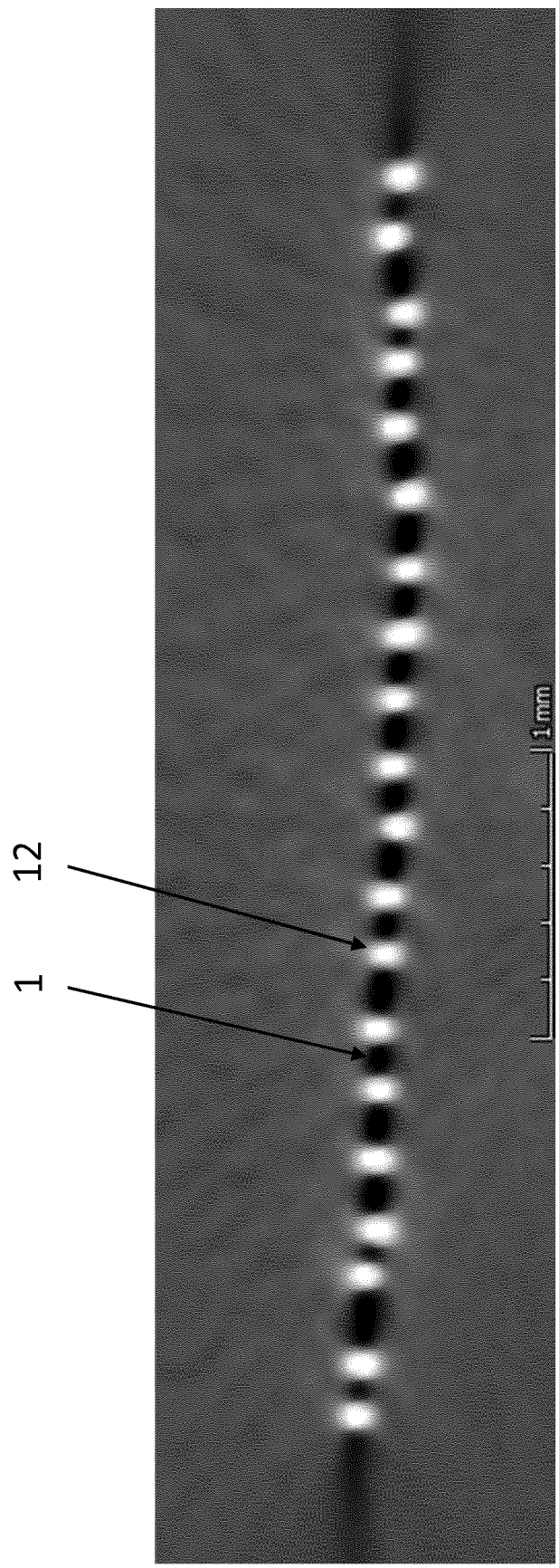
FIG. 19 shows an alternative X-ray image of a feedthrough.

The effect of polishing artefacts is particularly clear when viewing X-ray images (as polishing is not required for taking X-ray images). X-ray images are shown in FIGS. 18 and 19. FIGS. 18 and 19 are CT Scans (X-rays) of 0.002 inch (50 μm) diameter wires 1 in ZTA ceramic matrix 12.

The length of the image in FIG. 18 is about 2.4 mm (0.1 inch). The shadows and light pattern of the wires are an artefact of the X-ray technique which makes the diameter of the wires appear slightly larger than reality. However, it can clearly be seen that the wires are virtually parallel and straight over the entire visible 2.4 mm length.

FIG. 19 shows the in-plane positional accuracy is approximately within 0.0005 inch (12.7 μm), which is discussed in more detail below with reference to FIGS. 20 to 22.

Example Precision Conductor Placement

Figure 20:
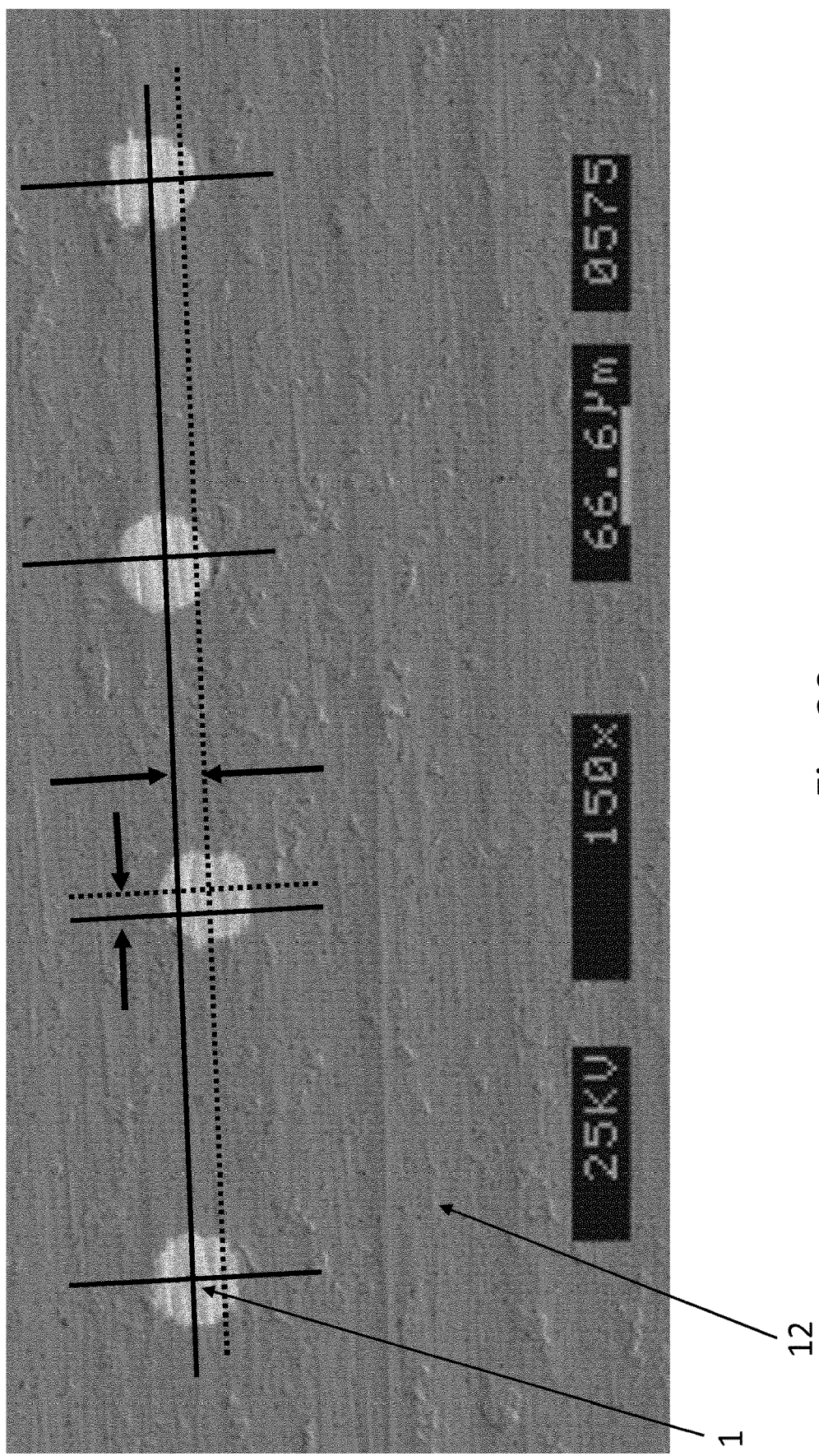
FIG. 20 shows an SEM micrograph of a cut section of a feedthrough.

FIG. 20 shows a conductor position tolerance of +/−50 microns with a conductor diameter of 50 microns. In FIG. 20 Pt pins 1 having a diameter of 0.002 inch (50 μm) are shown in a ZrO2 insulating ceramic 12. The surface is diced and unpolished. The solid lines correspond to a "perfect" or desired position and the dotted lines correspond to the measured position. These measurements demonstrate deviation from the desired position of <0.0005 inch (12.7 μm) within y-plane (left right as shown in FIG. 20). These measurements also demonstrate deviation from the desired position of <0.0008 inch (20.3 μm) within x-plane (up down as shown in FIG. 20).

Figure 21:
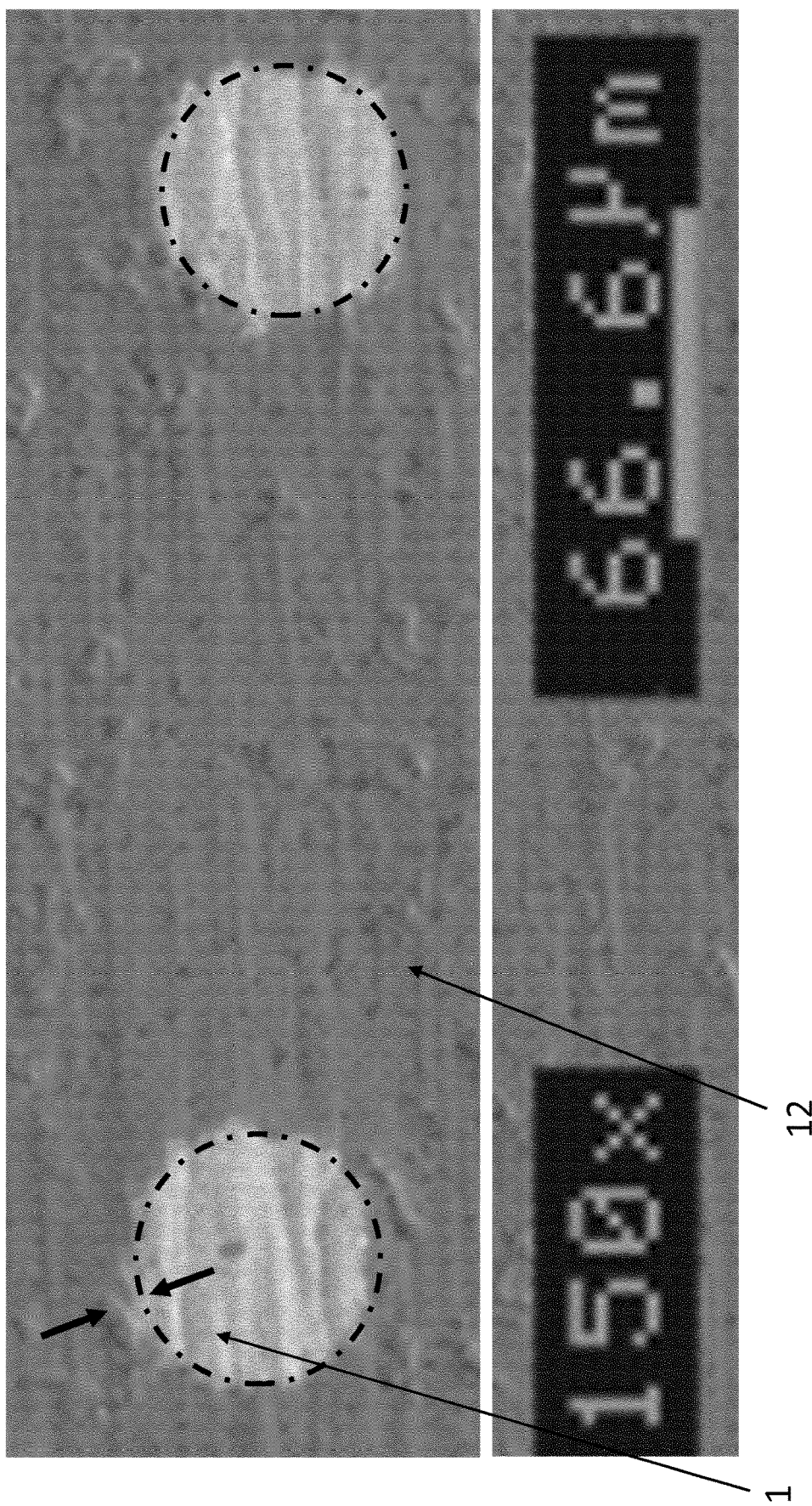
FIG. 21 shows an enlarged view of the SEM micrograph of FIG. 20.

FIG. 21 shows 2 thou diameter Pt pins in ZrO₂ ceramic body. The surface is diced and unpolished. In FIG. 21 the majority of deviation from "perfect" or desired position (indicated by dotted line) is a result of surface condition artefacts from dicing process due to soft nature of Pt. The deviation from the desired position is <0.0002 inch (5.1 μm).

Figure 22:
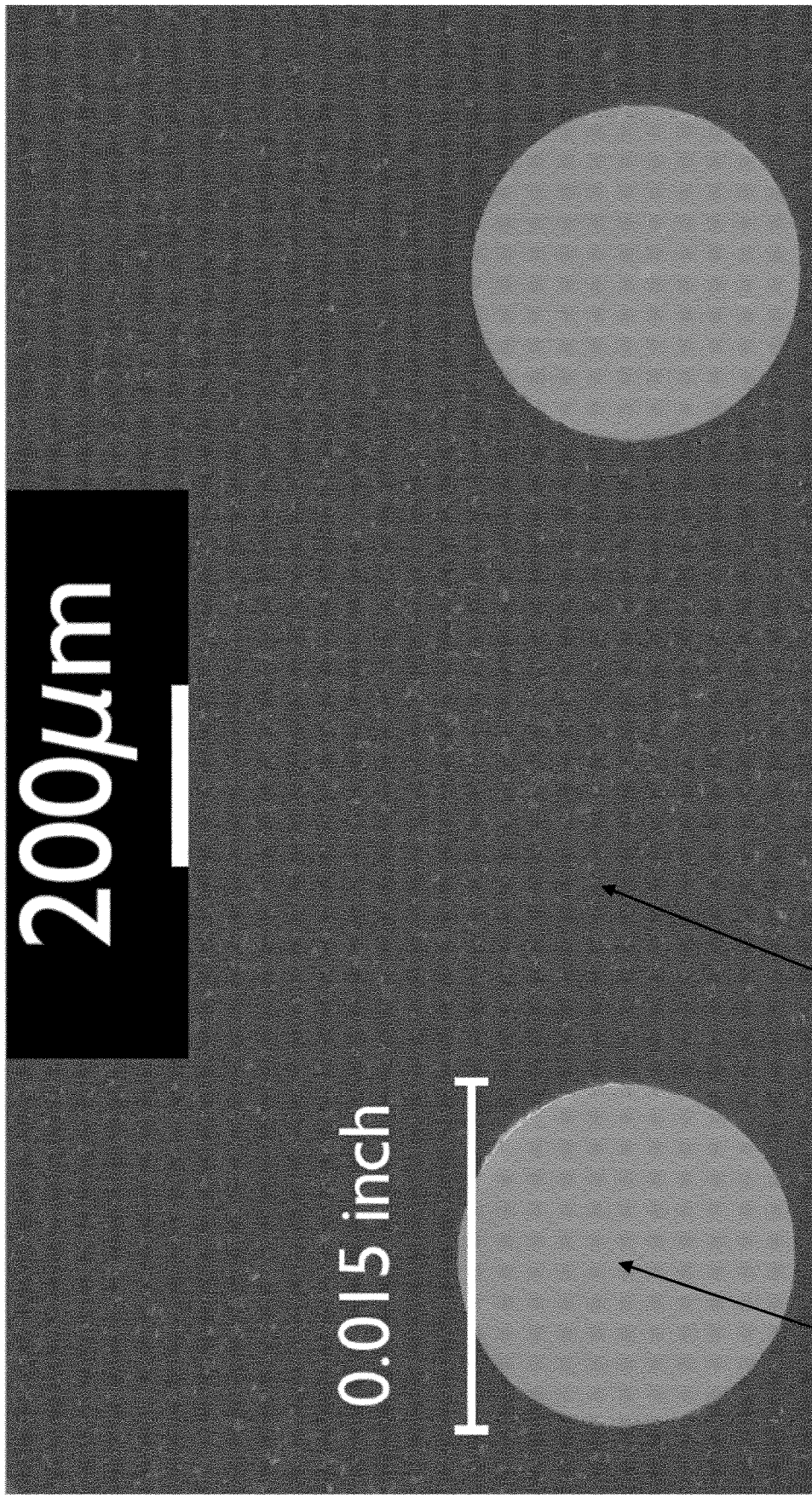
FIG. 22 shows an SEM micrograph of a cut section of a feedthrough.

FIG. 22 shows 0.015 inch (381 μm) diameter Pt pins in ZTA ceramic body. Again, the surface is diced and unpolished. In this example, no deviation from "perfect" or desired position is observable.

As will be apparent, with better control of minimum design spacing between electrical pathways, a designer can design pathways closer together, achieving greater miniaturization. It is therefore apparent that as the disclosed method allows more precise placement of the conductors, it therefore simultaneously allows the conductors to be placed closer together in a feedthrough design.

Example Conductor Densities

Conductor-to-conductor spacings of 10 thou using 2 thou diameter wires has been demonstrated. In this example 120 conductors were incorporated into the feedthrough at this conductor density. This is a significant improvement on the prior art resulting in a 5× overall reduction in the feedthrough area.

As will be apparent this corresponds to a density or 1 conductor per 100 thou$^2$.

In further examples (using 2 thou diameter wires) conductor-to-conductor center-to-center spacings of 235 microns (235 μm, 9.2 thou) has been demonstrated. In other examples conductor-to-conductor center-to-center spacings of 200 microns (200 μm, 7.9 thou) has been demonstrated. In yet further examples, conductor-to-conductor center-to-center spacings of 135 microns (135 μm, 5.3 thou) has been demonstrated. In another example, conductor-to-conductor center-to-center spacings of 100 microns (100 μm, 3.9 thou) has been achieved. In another example, conductor-to-conductor center-to-center spacings of 93 microns (93 μm, 3.66 thou). These spacings correspond to conductor densities of 1 conductor per 85 thou$^2$, 1 conductor per 62 thou$^2$, 1 conductor per 28 thou$^2$, 1 conductor per 15 thou$^2$, and 1 conductor per 13 thou$^2$, respectively.

Therefore, in examples conductor center-to-center spacings of the order of 4.8 thou or less corresponding to conductor densities of 1 conductor per 23 thou$^2$ have been achieved. In other examples, it is expected that conductor center-to-center spacings of 90 microns (90 μm, 3.5 thou) corresponding to conductor densities of 1 conductor per 12 thou$^2$ or even 1 conductor per 9 thou$^2$ can be achieved using the described methods.

FIG. 21 shows an SEM micrograph of a feedthrough (produced in accordance to the method and materials of Example 1) having 2 thou (50.8 μm) diameter conductors in a ceramic body. As the ceramic matrix is very hard it is difficult to polish, accordingly the visible porosity and scrub-offs are artefacts of the polishing process and not features of the feedthrough. In the image of FIG. 21, the distance a is 2 thou (50.8 μm) and the distance b is also 2 thou (50.8 μm). As will also be apparent, the conductors have a diameter of 2 thou (50.8 μm). As will also be apparent, the minimum distance between the surfaces of adjacent electrical conductors, through a planar cross-section of the ceramic body, is 2 thou (50.8 μm). Therefore, in this feedthrough the conductor-to-conductor center-to-center spacings are 4 thou (101.6 μm). This corresponds to a density of 1 conductor per 16 thou$^2$ (10,323 μm$^2$).

Accordingly, FIG. 21 demonstrates the achievement of a feedthrough having the combination of small conductor diameters, small minimum distance between the surfaces of adjacent electrical conductors, small conductor-to-conductor center-to-centre spacings, and high conductor density. It was possible to achieve this feedthrough using the present methods as the low pressure casting techniques enable lower diameter (i.e. more fragile) conductors to be used with a reduced risk of distortion during formation of the assembly.

Example Conductor Thinnesses/Thicknesses

Conductors having a diameter as small as 0.002 inch have been used in the described method to form a feedthrough. It is anticipated that conductors having a thicknesses as small as 0.001 inch may readily be used in the described method to form a feedthrough. Further, it is expected that conductors thinner than 0.001 inch may be used in the described method to form a feedthrough.

In certain circumstances use of thinner conductors may be preferred.

In other circumstances use of thicker conductors may be preferred. In particular, when the conductors are thicker they may support greater electrical requirements. For example, greater voltages and/or current requirements.

FIG. 12 shows a polished cross section of a 380 μm (15 mils) diameter platinum pin 33 co-sintered in an alumina matrix 34. FIGS. 11 and 12 show that the present disclosure enables use of multiple sized conductors (wires/pins) embedded and co-sintered in a fully dense ceramic matrix which is hermetic through the length of the embedded conductors.

Example Hermeticity Testing

The standard dimension and high density feedthroughs made through this process are hermetic to <1×10$^{-9}$ mbar-l/sec after the thermal shock (−60° C. to 200° C. 5 cycles).

In an example, a hermeticity of <1×10$^{-10}$ mbar-l/sec was measured. In a further example, a hermeticity of <1×10$^{-11}$ mbar-l/sec was measured. These measurements correspond to an excellent hermetic seal.

In measuring these hermeticities the protocol of MIL-STD-883 test method 1014 and test condition $A_4$ was employed.

Example Conductivity Testing

The resistivity/conductivity of 0.015 inch (381 μm), diameter Pt(90% wt)/Ir(10% wt) pins was measured. The data is reproduced in the table below. As can be seen, the measured conductivity is high whilst the measured resistivity is low. For example, the resistivity is approx. ⅕th of that reported by Kyocera document US2013/0032382 (comparing to 5% composition in Table 5; NB the prior art uses the units of ohm·m and the data below uses the units of ohm·cm).

| Sample | Average resistivity (Ω · cm) | Average conductivity (S/cm) |
| --- | --- | --- |
| Sintered | 4.00742E−05 | 25187.04809 |
| Green | 3.16756E−05 | 31648.54812 |

Example Precision Conductor Placement—Parallelism of Pins

In forming a feedthrough using the disclosed method it has been possible to achieve a feedthrough having conductors which are parallel to within <0.5°. This is so for feedthroughs having a thickness from 750 microns (750 μm, 30 thou) to 1.6 mm (63 thou).

Example Feedthrough Thicknesses

Using the disclosed method feedthroughs having thicknesses ranging from 750 microns (750 μm, 30 thou) to 1.6 mm (63 thou) have been prepared. These feedthroughs have good hermeticity, as described above.

As will be apparent to the skilled person, a wide range of thicknesses of feedthrough can be prepared using the disclosed method. However, for certain applications it may be necessary to make the feedthrough a certain thickness in order to achieve a desired hermeticity.

Determining Conductor Densities

Figure 25:
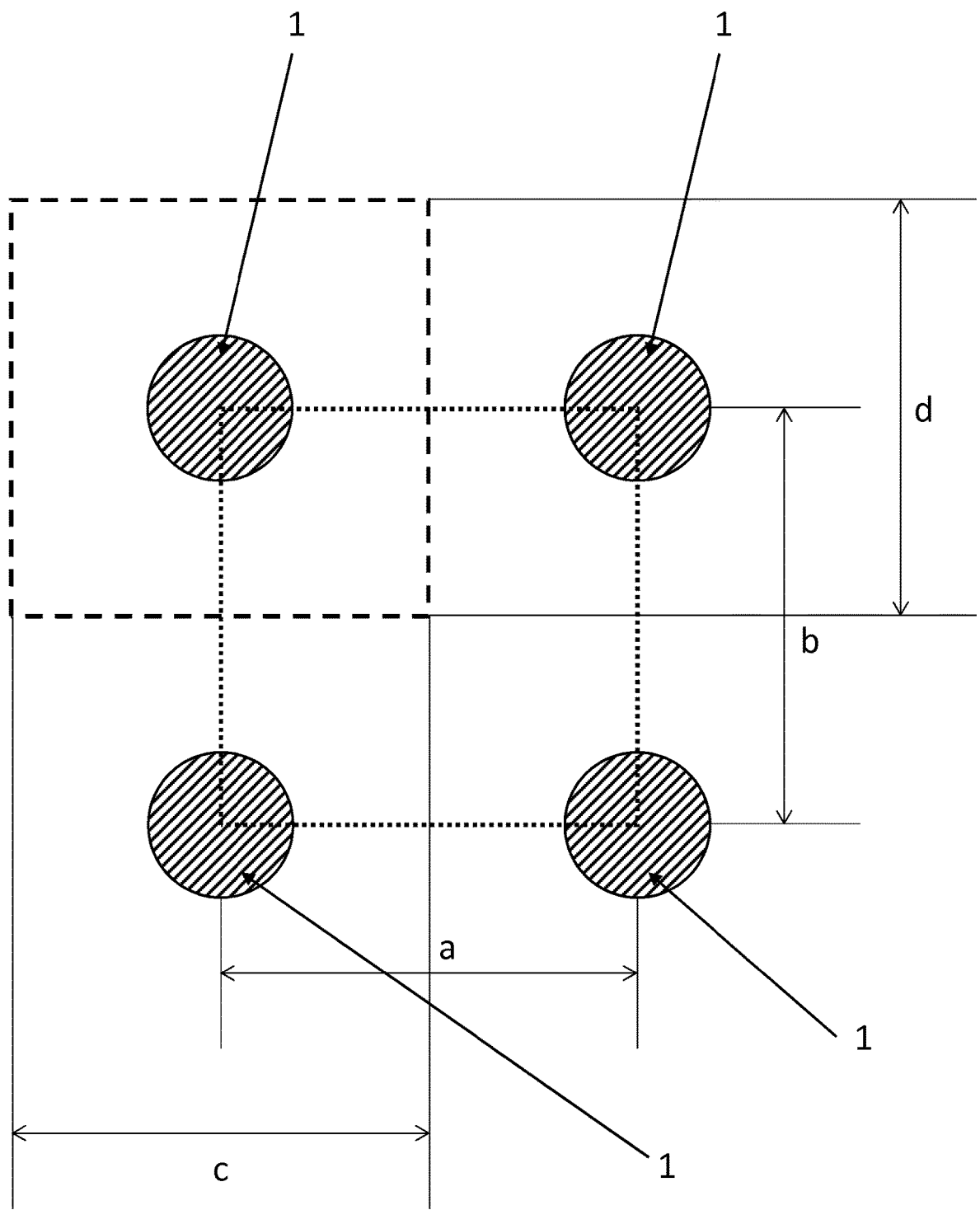
FIG. 25 shows a mathematical method for calculating conductor densities.
Figure 26:
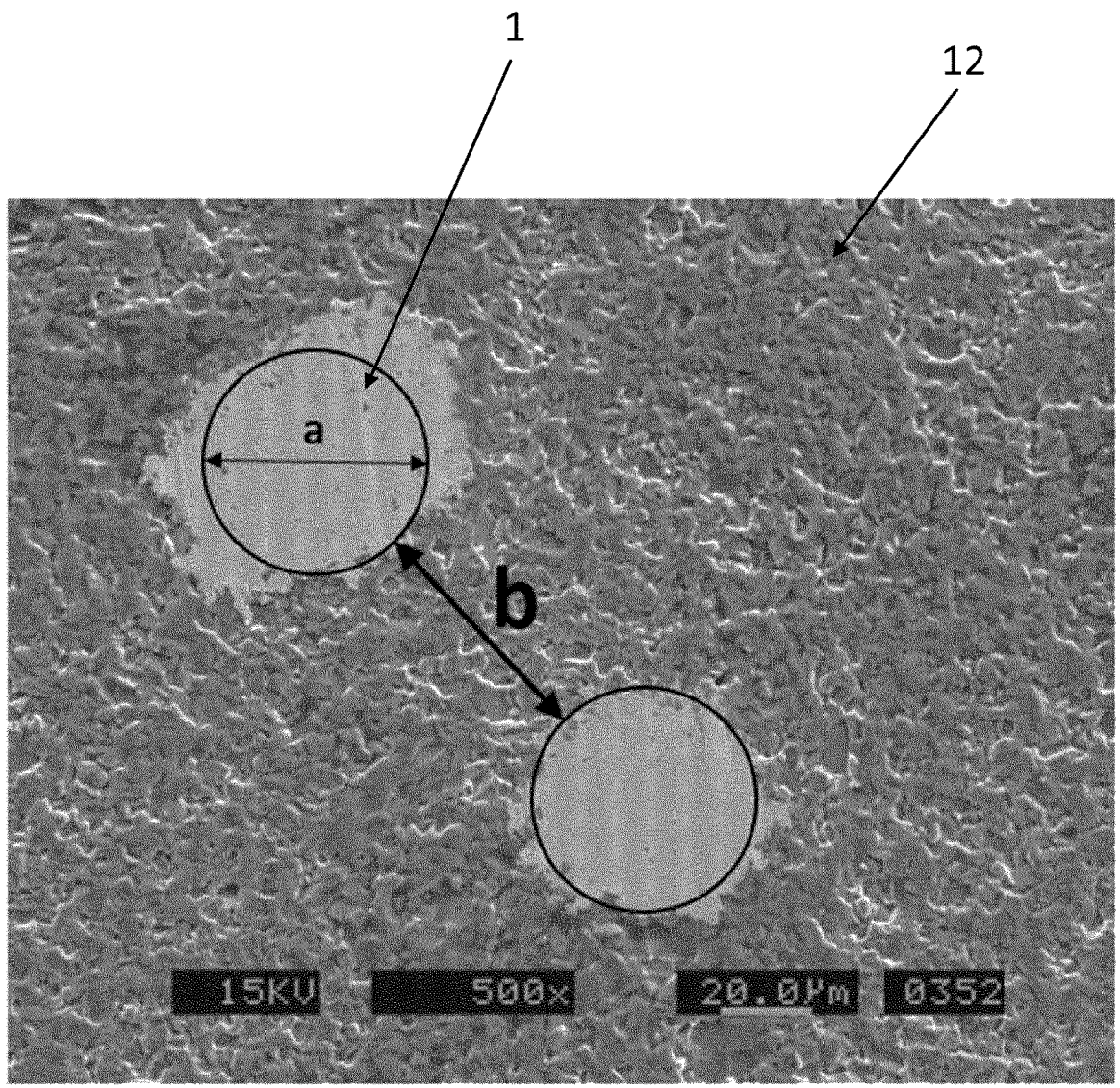
FIG. 26 shows an SEM micrograph of a cut section of another feedthrough.

A mathematical method for determining conductor densities is illustrated with reference to FIG. 25. In FIG. 25 four conductors 1 are shown. The view is that of a cross-section through a feedthrough.

The conductor density can be determined by conceptually analysing the square with sides of length a and b. As the square has a conductor in each corner, the conductors are given a ¼ value (each conductor lying in four conceptually similar squares) and the conductor density is one conductor per ab AREA. For example, if a=4 thou and b=4 thou, the density would be one conductor per 16 thou².

Of course, the conductor density could similarly be calculated using the square having sides c and d (which is equal in size to the square having sides a and b). In this case the square cd also includes one conductor and the density would be one conductor per cd AREA. For example, if c=4 thou and d=4 thou, the density would be one conductor per 16 thou².

Although not shown, conductors on edges of areas would count as ½ within a given area.

Using the present method it is possible to produce feedthroughs with high densities over large cross-sectional areas. For example, areas greater than 23 (0.014838), 100 (0.064516), 250 (0.16129), 500 (0.32258), 1000 (0.64516), 2000 (1.29032), 4000 (2.58054), 6000 (3.87096), 10000 (6.4516) thou² (mm²).

Final Definitions

When used in this specification and claims, the terms "comprises" and "comprising" and variations thereof (e.g. "include" and "including") mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A feedthrough including:
   a ceramic body; and
   a plurality of electrical conductors embedded in the ceramic body,
   wherein the density of the electrical conductors exceeds 1 conductor per 23 thou² (14,839 µm²) through a planar cross-section of the ceramic body, wherein each of plurality of electrical conductors comprises a solid metal wire.

2. A feedthrough as claimed in claim 1, wherein each of the plurality of electrical conductors is parallel relative to each other within 2° or each of the plurality of electrical conductors is evenly spaced apart within a tolerance of ±5% or 0.002" (50.8 µm) whichever is greater.

3. A feedthrough as claimed in claim 1, in which the plurality of elongate electrical conductors includes at least one planar array of elongate electrical conductors defining a plane, and at least one elongate electrical conductor non-parallel with said plane.

4. A feedthrough as claimed in claim 1, in which the ceramic body includes one or more walls extending from a base, and at least one of said plurality of elongate electrical conductors is mounted to traverse the ceramic body from the base to said one or more walls.

5. A feedthrough as claimed in claim 1, wherein the ceramic body is monolithic.

6. A feedthrough as claimed in claim 1, wherein the density of the electrical conductors is not more than 1 conductor per 9 thou² (5,806 µm²) through a planar cross-section of the ceramic body.

7. A feedthrough as claimed in claim 1, wherein a surface of a first electrical conductor is at least 40 µm (0.00157 inch) apart, through a planar cross-section of the ceramic body, from a surface of a second electrical conductor.

8. A feedthrough as claimed in claim 1, wherein a surface of a first electrical conductor is within 0.0038 inch (96.5 µm), through a planar cross-section of the ceramic body, of a surface of a second electrical conductor.

9. A feedthrough as claimed in claim 1, wherein the density of the electrical conductors is no more than 1 conductor per 9 thou² (5,806 µm²) through a planar cross-section of the ceramic body; and the diameter of the electrical conductors is between 0.0004 inch (10.2 µm) and 0.020 inch (508 µm).

10. A medical device including the feedthrough of claim 1.

11. A green body for co-firing to form a feedthrough including:
    a green ceramic body; and
    a plurality of electrical conductors embedded in the ceramic body,
    wherein the density of the electrical conductors exceeds 1 conductor per 23 thou² (14,839 µm²) through a planar cross-section of the green ceramic body and each of plurality of electrical conductors comprises a solid metal wire.

12. A method of forming an assembly of electrical conductors at least in part embedded in a ceramic or a ceramic precursor matrix, the method comprising:
    fixedly attaching a plurality of elongate electrical conductors to a frame to form a conductor-frame assembly including a plurality of elongate electrical conductors;
    introducing a fluid ceramic or ceramic precursor into a cavity at a pressure of less than 2 atmosphere (absolute) to form a self-supporting body, wherein the self-supporting body embeds at least part of the elongate electrical conductors.

13. The method, as claimed in claim 12, further comprising:
    fixedly attaching each of a first group of elongate electrical conductors by ends thereof to a first group of frame parts
    securing a second group of frame parts in fixed relationship to the first group of frame parts
    fixedly attaching each of a second group of elongate electrical conductors by one end to the second group of frame parts, and by another end to either one of the first or second group of frame parts.

14. The method as claimed in claim 12, in which fixedly attaching a plurality of elongate electrical conductors to the frame includes using diffusion bonding; mechanical fastening; adhesives; laser assisted diffusion bonding; or welding to join the elongate electrical conductors to metallic regions of the frame.

15. The method as claimed in claim 12, wherein the fluid ceramic or ceramic precursor is introduced by slip casting, gel casting, low pressure-low viscosity thermoplastic injection moulding, fluidized bed direct transfer, low stress casting, zero pressure casting, casting by gravity feed or casting without application of external pressure.

16. The method as claimed in claim 13, wherein the fluid ceramic or ceramic precursor is introduced by slip casting, gel casting, low stress casting, zero pressure casting, casting by gravity feed or casting without application of external pressure.

17. The method as claimed in claim 12, in which the body is formed in the cavity as a green ceramic body which is fired to co-sinter the ceramic on to the elongate electrical conductors to provide a hermetic join between ceramic and elongate electrical conductors.

18. A feedthrough produced by a method according to claim 12.

19. The method as claimed in claim 12, wherein the method forms a feedthrough in which one or more of the plurality of electrically conductive connectors extend from one surface of the self-supporting body to another surface of the self-supporting body.

\* \* \* \* \*